US012642534B2

(12) United States Patent
Buchanan

(10) Patent No.: US 12,642,534 B2
(45) Date of Patent: Jun. 2, 2026

(54) SECONDARY DEVICE HOLDER AND COMPRESSION SYSTEM, METHOD OF MAKING AND USING THE SAME

(71) Applicant: William P Buchanan, Wilmington, NC (US)

(72) Inventor: William P Buchanan, Wilmington, NC (US)

( * ) Notice: Subject to any disclaimer, the term of this patent is extended or adjusted under 35 U.S.C. 154(b) by 661 days.

(21) Appl. No.: 17/688,767

(22) Filed: Mar. 7, 2022

(65) Prior Publication Data

US 2022/0183699 A1 Jun. 16, 2022

Related U.S. Application Data

(63) Continuation of application No. 17/397,794, filed on Aug. 9, 2021, now Pat. No. 11,272,941.

(Continued)

(51) Int. Cl.
*A61B 17/132* (2006.01)
*A61B 17/122* (2006.01)
(Continued)

(52) U.S. Cl.
CPC ........ *A61B 17/1327* (2013.01); *A61B 17/122* (2013.01); *A61B 17/135* (2013.01);
(Continued)

(58) Field of Classification Search
CPC . A61B 17/1327; A61B 17/135; A61B 17/122; A61B 17/3421; A61B 17/3492;
(Continued)

(56) References Cited

U.S. PATENT DOCUMENTS 5,514,155 A * 5/1996 Daneshvar ......... A61B 17/1325
602/53
5,599,305 A 2/1997 Hermann et al.
(Continued)

OTHER PUBLICATIONS

Aoi et al., Distal transradial artery access in the anatomical snuffbox for coronary angiography as an alternative access site for faster hemostasis, Catheter Cardiovasc Interv., Feb. 6, 2019, pp. 1-7, Wiley, https://doi.org/10.1002/ccd.28155.
(Continued)

*Primary Examiner* — Brigid K Byrd
(74) *Attorney, Agent, or Firm* — Scott J. Hawranek; Messner Reeves LLP

(57) ABSTRACT

A device that holds a radial sheath, catheter or similar structure in place during surgical procedures. The device has a strap configured to fit around a patient's wrist and a two-part section that includes a sheath holder or clamp. The clamp is configured to accept a free end of the sheath or other device and to allow the physician access to the open end of that sheath so that they can insert instruments through it. The second section contains a compression device that, when positioned over the puncture site, can be expanded such that it provides pressure and patent hemostasis to the site to stop bleeding. Adhesive surfaces with peel away releasable liners on one or more surfaces of the device allow the flap featuring the compression balloon to be folded over onto the flap containing the sheath clamp and hold it in place.

18 Claims, 27 Drawing Sheets

Related U.S. Application Data

(60) Provisional application No. 63/062,580, filed on Aug. 7, 2020.

(51) Int. Cl.

| | |
|---|---|
| *A61B 17/135* | (2006.01) |
| *A61B 17/34* | (2006.01) |
| *A61B 17/12* | (2006.01) |

(52) U.S. Cl.
CPC .................... *A61B 17/3421* (2013.01); *A61B 2017/12004* (2013.01); *A61B 2017/3492* (2013.01)

(58) Field of Classification Search
CPC ........... A61B 2017/12004; A61B 2017/00557; A61M 25/02
See application file for complete search history.

(56) References Cited

U.S. PATENT DOCUMENTS

| | | | | |
|---|---|---|---|---|
| 5,643,315 | A * | 7/1997 | Daneshvar | ........ A61F 13/01034 606/202 |
| 6,638,296 | B2 | 10/2003 | Levinson | |
| 6,846,321 | B2 | 1/2005 | Zucker | |
| 7,223,266 | B2 | 5/2007 | Lindenbaum et al. | |
| 7,927,295 | B2 * | 4/2011 | Bates | ...................... A61B 17/12 602/53 |
| 9,867,625 | B2 | 1/2018 | Finkielsztein et al. | |
| 10,213,213 | B2 | 2/2019 | Pancholy et al. | |
| 10,470,778 | B2 | 11/2019 | Corrigan, Jr. | |
| 11,116,516 | B2 | 9/2021 | Castelli et al. | |
| 2005/0165445 | A1 * | 7/2005 | Buckman | ................ A61F 13/00 606/213 |
| 2012/0150215 | A1 | 6/2012 | Donald | |
| 2014/0012120 | A1 * | 1/2014 | Cohen | ................ A61B 5/02042 600/371 |
| 2014/0288590 | A1 | 9/2014 | Kruk | |
| 2015/0018869 | A1 * | 1/2015 | Benz | ..................... A61B 17/135 606/203 |
| 2015/0224285 | A1 * | 8/2015 | Howell | ................. A61M 25/02 604/174 |
| 2016/0038154 | A1 * | 2/2016 | Cohen | .................. A61B 17/135 606/202 |
| 2017/0215892 | A1 * | 8/2017 | Pancholy | ........... A61B 17/1325 |
| 2019/0133602 | A1 | 5/2019 | Kiemeneij et al. | |
| 2019/0314027 | A1 | 10/2019 | Clark | |
| 2019/0314035 | A1 | 10/2019 | Hopkinson et al. | |
| 2020/0275936 | A1 | 9/2020 | O'Brien et al. | |
| 2021/0186521 | A1 * | 6/2021 | Kawaura | ........... A61B 17/1325 |
| 2021/0204953 | A1 | 7/2021 | Kawaura et al. | |
| 2021/0251636 | A1 * | 8/2021 | O'Brien | ............. A61B 17/1325 |
| 2023/0012524 | A1 * | 1/2023 | Kawaura | ............... A61F 13/024 |

OTHER PUBLICATIONS

Chatelain et al., New Device for Compression of The Radial Artery After Diagnostic and Interventional Cardiac Procedures, Catheterization and Cardiovascular Diagnosis, 1997, pp. 297-300. Wiley-Liss, Inc., vol. 40, Geneva, Switzerland.

Chu et al., Update on Trasnradial Access for Percutaneous Transcatheter Visceral Artery Embolization, Korean Journal of Radiology, 2021, pp. 72-85, The Korean Society of Radiology, vol. 22(1), https://doi.org/10.3348/kjr.2020.0209.

Costa et al., Radial Compression Devices Used After Cardiovascular Interventions, Vascular Closure Devices, 2019, pp. 67-71, vol. 13, No. 4, Cardiac Interventions Today, Messina, Italy.

Danillo et al., Distal transradial access as default approach for coronary angiography and interventions, 2019, pp. 513-519, vol. 9, No. 5, Cardiovascular Diagnosis and Therapy, http://dx.doi.org/10.21037/cdt.2019.09.06.

Kawamura et al., Impact of dedicated hemostasis device for distal radial arterial access with an adequate hemostasis protocol on radial arterial observation by ultrasound, Cardiovascular Intervention and Therapeutics, 2020, pp. 104-110, vol. 36, Springer, https://doi.org/10.1007/s12928-020-00656-4.

PreludeSYNCDISTAL Radial Compression Device, p. 2 Product Description, p. 3 Figure 2, p. 4 No. 6, 8-11 and Figure 3, Merit Medical Systems, Inc., South Jordan Utah.

PreludeSYNC EVO Radial Compression Device, p. 1, Merit Medical Systems, Inc., South Jordan Utah.

PreludeSYNC Radial Compression Device Reference Guide, p. 1, Merit Medical Systems, Inc., South Jordan Utah.

PreludeSYNC Radial Compression Devices Family, pp. 1-6, Merit Medical Systems, Inc., South Jordan Utah.

TR Band Radial Compression Device, pp. 1-3, 2019, Terumo Interventional Systems.

* cited by examiner

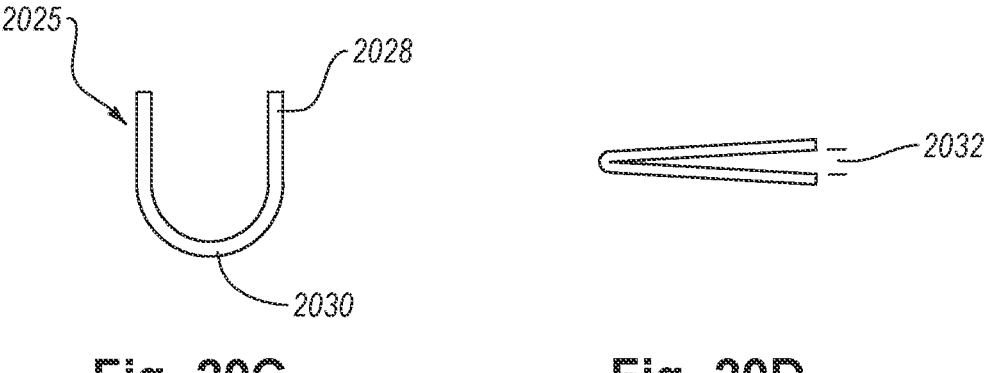
Fig. 20C          Fig. 20D

SECONDARY DEVICE HOLDER AND COMPRESSION SYSTEM, METHOD OF MAKING AND USING THE SAME

CROSS REFERENCE TO RELATED APPLICATIONS

This application is a continuation of U.S. patent application Ser. No. 17/397,794 filed on Aug. 9, 2021, which claims the benefit of U.S. Provisional Patent Application No. 63/062,580, filed on Aug. 7, 2020, the entire contents of each of the above-identified applications are hereby incorporated by reference as if fully set forth herein.

BACKGROUND OF THE INVENTION

Field of the Invention

The present disclosure is in the technical field of surgical devices. More particularly, the present disclosure relates to a medical device used by surgeons to assist them in inserting secondary devices, e.g., removing catheters and similar devices and with hemostasis of a patient's insertion site upon removal of the secondary devices.

Discussion of the Related Art

Minimally invasive surgeries have increasingly come to replace more traditional procedures involving open surgery with large incisions in the patient that can lead to painful and lengthy recovery times and increased infection rates. Minimally invasive surgeries have their origin in procedures performed by interventional radiologists. Specifically, angioplasty was one of the first minimally invasive surgical procedures to be widely used. In particular, a number of cardiac procedures can be performed using minimally invasive surgical procedures. Several these procedures involve inserting one or more secondary devices, e.g., a catheter or other instrument, into the patient's circulatory system via a small puncture wound.

In such cases, a sheath can be introduced into the patient's circulatory system via an artery such as the radial artery. The sheath is a hollow tube through which other instruments can be inserted into the patient. Typically, a surgeon inserts a guide wire into the sheath first and guides it to the desired location in the patient's body, often with the use of fluoroscopy. That guide wire is left in place while the surgeon inserts other instruments, e.g., catheters, into the patient. Surgeons use a variety of catheters for several different purposes and often have to use more than one type of catheter in a single surgical procedure. For example, some are merely used for diagnostic purposes while other catheters are designed to guide other instruments to a particular portion of the patient's body.

Currently, after the secondary device is inserted it is not secured in place or not adequately secured by current methods. For example, after use the secondary device can be inadvertently moved, removed or displaced during a procedure. Such movement can adversely impact the overall procedure, e.g., formation of a hematoma or trauma at the puncture site.

There exists a need in the field for a device that holds the secondary device, e.g., sheath, in place while the surgeon is passing instruments though the sheath and otherwise completing the surgical procedure.

SUMMARY OF THE INVENTION

Accordingly, the invention is directed to a radial secondary device and compressions device, method of making and using the same that substantially obviates one or more of the problems due to limitations and disadvantages of the related art.

An advantage of the invention is to provide a system that allows for rapid exchange of media.

Another advantage of the invention is to provide a single device that is configured to support a secondary device during a non-invasive surgical procedure and as a radial artery compression system.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a medical device is configured to hold a secondary device, e.g., radial sheath, catheter, guidewire and combinations of the same and the like, in place during surgical procedures and also configured as a compression system. The compression system is configured to obtain hemostasis once the secondary device is removed from the patient.

In another aspect of the invention, the medical device includes a patch, e.g., surgical adhesive patch, for supporting a secondary medical device during a non-invasive surgical procedure using a radial artery and for providing a desired degree of hemostasis to the radial artery after the non-invasive surgical procedure.

In yet another aspect of the invention, the medical device includes a first patch portion including a compression bladder in fluid communication with an inflation port or tube and, a first adhesive material arranged on a first surface of the first patch portion, wherein the first adhesive material is not arranged on the compression bladder and the first adhesive material is arranged under a first peel away sheet. The device further includes a second patch portion movably coupled to the first portion with a living hinge and the second patch portion includes a cutout region configured to allow access to a patient's puncture site, a second adhesive material arranged on a first surface of the second patch portion that is configured to adhere to the first adhesive material, a third adhesive material on an opposite second surface configured to adhere to the patient, and an anchor region configured to support a secondary device. The second adhesive material is arranged under a second peel away sheet and the third adhesive material is arranged under a third peel away sheet. The first portion is larger than the second portion and the first adhesive is configured to be adhered to the second adhesive material and the patient's skin. The compression bladder is configured to be inflated to a predetermined pressure to provide a desired degree of hemostasis to a patient's radial artery after a surgical procedural.

In still yet another aspect of the invention, the medical device includes a first portion including a first clamp, a compression bladder in fluid communication with an inflation port or tube, and a first adhesive material arranged on a surface of the first portion. The adhesive material is not arranged on the compression bladder; the first adhesive material is arranged under a first peel away sheet configured to be fully removed to expose the first adhesive material. The medical device also includes a second portion coupled to the first portion with a living hinge, the first portion is configured to be movably arranged over the second potion with the living hinge. The second portion includes a second clamp configured to engage the first clamp in a releasable configuration, a cutout region configured to allow access to a patient's puncture or insertion site of secondary device, and a second adhesive material arranged on a first surface of the second portion and configured to adhere to the patient. The second clamp is configured to support a secondary device during the non-invasive surgical procedure. The second adhesive material is arranged under a second peel away sheet. The first portion is larger than the second portion and the first adhesive is configured to be adhered to a surface of the second portion and the patient's skin. The compression bladder is configured to be inflated to a predetermined pressure to provide a desired degree of the hemostasis to the patient's radial artery after the secondary device is removed.

In yet another aspect of the invention, a medical kit includes a package containing a medical device as described herein and instructions for use.

In still yet another aspect of the invention, the medical device is configured as a surgical patch.

In yet another aspect of the invention the medical device includes a first portion including a compression bladder in fluid communication with an inflation port or tube and a first adhesive material arranged on a portion of a surface of the first portion under a first peel away sheet. The device further includes a second portion coupled to the first portion with a living hinge where the second portion includes a second adhesive material arranged under a second peel away sheet, a cut out region, and an anchor portion configured to receive a portion of the secondary device and configured to support the secondary device during the non-invasive procedure. The first portion is larger than the second portion and the first adhesive is configured to be adhered to a surface of the second portion and the patient's skin. The compression bladder is configured to be inflated to a predetermined pressure to provide a desired degree of the hemostasis to the patient's radial artery after the secondary device is removed.

In yet another aspect of the invention a method of using the medical device includes providing a medical device described herein. The method further includes locating a radial artery and cleaning the area around the located radial artery. A portion of the medical device is attached to a wrist of the patient such that the cut out region exposes the cleaned located radial artery and is positioned around a secondary device or partially around the secondary device. The method further includes supporting the secondary device with the anchor portion and/or clamp during a portion of the medical procedure. The method further includes attaching a portion of the medical device to another portion of the medical device. The method further includes inflating the compression bladder to a predetermined pressure to provide a desired degree of hemostasis to the patient's radial artery.

This Summary section is neither intended to be, nor should be, construed as being representative of the full extent and scope of the present disclosure. Additional benefits, features and embodiments of the present disclosure are set forth in the attached figures and in the description hereinbelow, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments supporting the claims. Thus, it is important that the claims be regarded as having a scope including constructions of various features of the present disclosure insofar as they do not depart from the scope of the methods and apparatuses consistent with the present disclosure (including the originally filed claims). Moreover, the present disclosure is intended to encompass and include obvious improvements and modifications of the present disclosure.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 20C illustrates a top view of clamp according to an embodiment of the invention.

FIG. 20D illustrates a side view clamp according to an embodiment of the invention.

DETAILED DESCRIPTION OF THE ILLUSTRATED EMBODIMENTS

Figure 1:
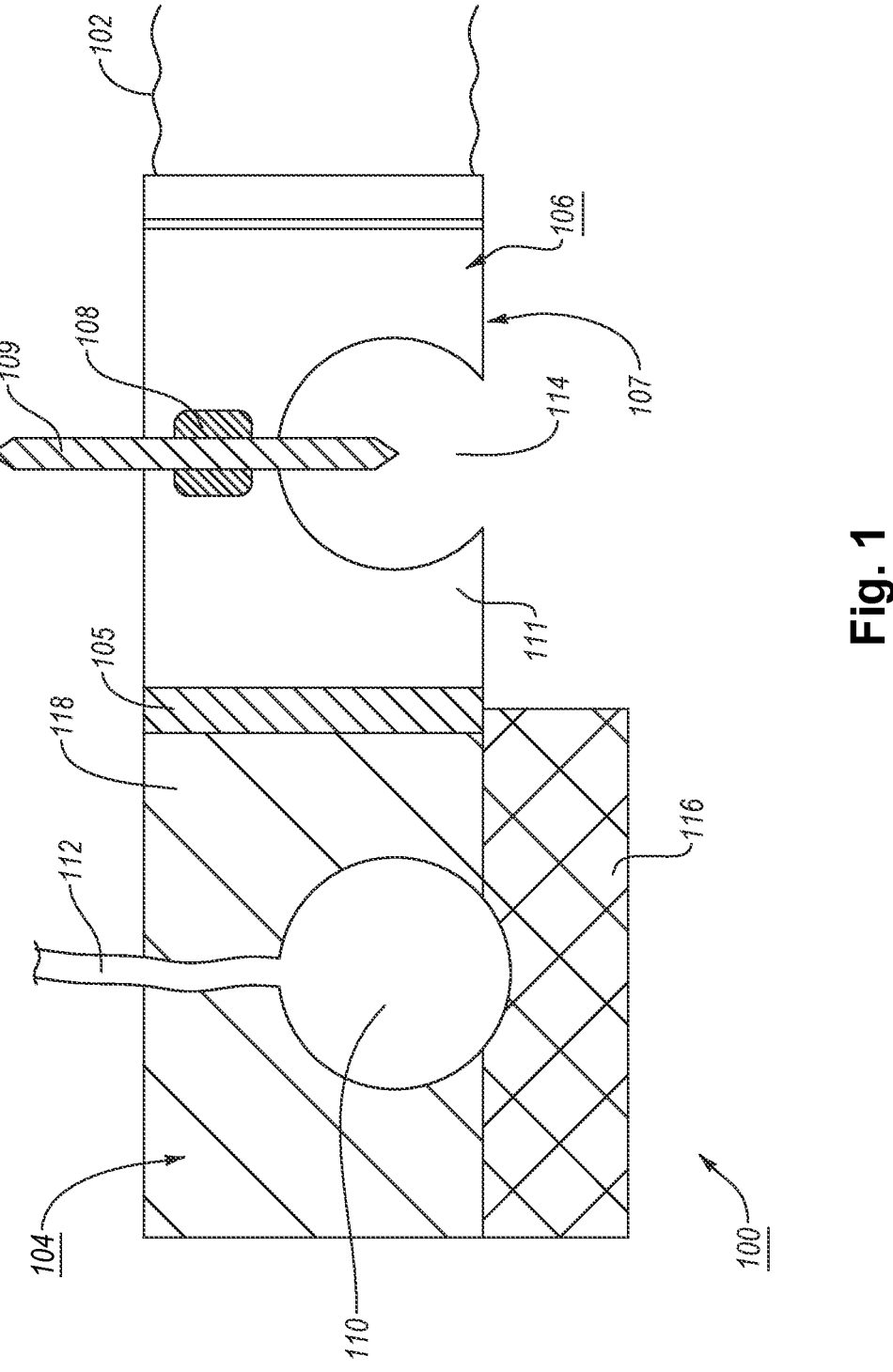
FIG. 1 illustrates an exemplary top plan view of a medical device according to an embodiment of the invention.

For the purposes of promoting an understanding of the principles of the present disclosure, reference will now be made to the exemplary embodiments illustrated in the drawings, and specific language will be used to describe the same.

Appearances of the phrases an "embodiment," an "example," or similar language in this specification may, but do not necessarily, refer to the same embodiment, to different embodiments, or to one or more of the figures. The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps unless explicitly stated otherwise.

In order to appreciate the present disclosure more fully and to provide additional related features, the following references are incorporated therein by reference in their entirety:

(1) U.S. Pat. No. 5,599,305 issued to Hermann, et al., which discloses a catheter introducing system, includes an introducer catheter comprising a flexible sheath having a hemostasis valve and an obturator having a steering mechanism operated by a proximal actuator handle. The catheter introducer system will usually be introduced with the obturator inside of the flexible sheath so that the obturator can effect steering by laterally deflecting the distal end of the combined sheath and obturator. Such catheter introducing systems are particularly useful for large diameter sheaths which are not readily introduced over guide wires. A first exemplary hemostasis valve comprises a compressed foam insert having an axial lumen therein. A second exemplary hemostasis valve comprises an elastomeric insert which receives and seals over the catheter.

(2) U.S. Pat. No. 6,638,296 issued to Levinson, which discloses a hemostatic device, including an adhesive patch and a hemostatic pad. The adhesive patch includes an adhesive backing, an absorbent pad attached to a bottom surface of the adhesive backing, and a flexible disc attached to a top surface of the adhesive backing. The adhesive backing includes a central portion and two adhesive ends extending from the central portion. The hemostatic pad is attached to a bottom surface of the absorbent pad. A hemostatic effective amount of hemostatic agent is attached to a bottom surface of the hemostatic pad. The hemostatic pad defines an aperture at an approximately central point and an elongated cut extending from the aperture. The patch defines an associate aperture and an elongated cut above the aperture and the elongated cut of the hemostatic pad. The apertures and the cuts allow the passage of an indwelling tubular element at the puncture wound.

(3) U.S. Pat. No. 6,846,321 issued to Zuker, which discloses a method for hemostasis of an artery having a puncture after arterial catheterization, the catheterization using an introducer sheath, the method including the steps of inserting into an artery a catheter introducer having a forward end and a balloon adjacent to the forward end prior to arterial catheterization, following arterial catheterization and removal of a catheter from the catheter introducer, retracting the catheter introducer such that the forward end thereof lies exterior of the artery adjacent a puncture in the wall of the artery, inflating the balloon, thereby causing inward collapse of the forward end of the catheter introducer, thereby defining an enhanced surface area surrounded by the balloon adjacent the puncture for hemostasis, and following hemostasis, deflating the balloon and removing the catheter introducer from the patient. An introducer sheath suitable for use in the method is also described and claimed.

(4) U.S. Pat. No. 7,223,266 issued to Lindenbaum, et al., which discloses a method for producing hemostasis of an artery of a patient having a puncture following arterial catheterization including introducing a hemostasis device including at least one electrode into the vicinity of the puncture, supplying an electric current to the at least one electrode, thereby heating blood in the vicinity of the puncture and causing coagulation of the blood and subsequently removing the hemostasis device from the patient.

(5) U.S. Pat. No. 9,867,625 issued to Finkielsztein, et al., which discloses a vascular compression apparatus and method for applying pressure onto an area of a patient generally including a blood vessel and a wound site, such as a blood vessel puncture after a cannulated procedure, for the purpose of controlling bleeding and achieving hemostasis.

(6) U.S. Pat. No. 10,213,213 issued to Pancholy, et al., which discloses a hemostatic device provided to stop bleeding at a puncture site on an artery of a patient, the device comprising a transparent flexible band to be wrapped at the site where the bleeding is to be stopped, a curved compression member having an inner peripheral side and possessing a first curved portion in its first half and a second curved portion in its second half, a first balloon provided on the inner peripheral side in the first half of the curved compression member and a second balloon provided on the inner peripheral side in the second half of the curved compression member. The bleeding from a first artery is stopped by compressing the first artery at the puncture site using inflation of the first balloon and blood flow in the first artery is increased by compression of a second artery using inflation of the second balloon.

(7) U.S. Pat. Appl. Publication No. 2019/0314027 issued to Clark, which discloses an accessory for a VasoStat™ hemostasis device that locks the plunger within the cylinder through which the plunger travels by restricting disengagement of ratcheted wings affixed to the plunger. The accessory may be repositioned or removed so that the ratcheted wings may be disengaged and the plunger may be retracted within the cylinder.

When integrated into the plunger, the accessory may be configured to move between a first unlocked position and a second locked position. As a separate component, the accessory is configured to be positioned over and locked into position on the hemostasis device, such as the central stem of the plunger.

In one embodiment, the medical device is a surgical patch for supporting a secondary medical device during a non-invasive surgical procedure using a radial artery and providing a desired degree of hemostasis to the radial artery after the non-invasive surgical procedure. The medical device includes a first portion movably coupled to a second portion with a living hinge. The living hinge may be produced by molding, cutting, stamping, thinning, reducing and/or perforating an amount of material at the desired bend point, thereby creating a hinge portion. The term patch means any sterile material thermoplastic material, e.g., a plastic material, a polymer material, and combinations thereof. In one embodiment, the patch is visually transparent to allow a clinician to see through the patch to the insertion site or other area the patch is covering. The adhesive material is also transparent or arranged to allow for semi-transparency or transparency in order to allow the clinician to see through the patch.

In one embodiment, the adhesive is configured in any geometric configuration including but not limited to one or more of separated line patterns, full coverage, circle patterns, and combinations therefor.

In a preferred the patch and bladder is transparent to a allow a clinician to see through and to the patient's skin.

In one embodiment, the medical device is sized to work with a surgical procedure that uses a secondary device in a femoral artery.

In one embodiment, the medical device is sized to work with a surgical procedure that uses a secondary device in a brachial artery.

In one embodiment, the medical device is sized to work with a surgical procedure that uses a secondary device in a radial artery.

In this embodiment, the first portion includes a compression bladder in fluid communication with an inflation port or tube. The compression bladder can include an inflatable thermoplastic material. In one embodiment, the compression bladder and/or inflation thereof is described with reference to U.S. Pat. No. 9,867,625, which is hereby incorporated for these teachings. The first portion includes a first adhesive material arranged on a portion of a surface of the first portion under a first peel away sheet. The first peel away sheet covers the first adhesive and protects it until the peel away sheet is removed.

The second portion is configured to be arranged over a first portion with the living hinge. The second portion includes a second adhesive material arranged under a second peel away sheet. The second adhesive material is configured to be adhered to the skin of a patient. The second portion includes a cut out region configured to provide access to a puncture site of a patient, e.g., the radial artery, and an anchor portion configured to receive and/or support a portion of the secondary device during the non-invasive procedure. The anchor portion can include a snap and fit system configured to secure the secondary device or any other anchor portion as described herein. The first portion is configured to be secured to the second portion and the second portion is secured to the patient. The compression bladder is configured to be inflated to a predetermined pressure to provide a desired degree of hemostasis to a patient's radial artery after a surgical procedural and the secondary device is removed.

In one embodiment, a clamp or other device is configured to support a portion the secondary device, e.g., sheath via a flush port of the sheath during the procedure. The clamp can have any geometry, e.g., paperclip, bobby pin, open end and closed end.

In one embodiment, the first portion and second portion are separate portions and not coupled with a living hinge. That is, the first portion is used and subsequently the second portion is arranged over or near the first portion.

Optionally and/or alternatively, a second patch or covering can be arranged over the second portion and/or the first portion to aid in securing the second portion and the first portion to the patient.

In one embodiment, the first portion is oversized to cover the entire second portion. Each of the first portion and the second portion include transparent material. In one embodiment, the first portion is sized to be larger than the second portion. The first portion and/or the second portion can include a surgical gauze or sponge like material configured to absorb blood. In one embodiment, the first portion and/or second portion can include a pharmacological agent. The pharmacological agent can include one or more of hemostasis agent, coagulating agent, anti-bacterial agent, pain relief agent, anti-swelling agent, and combinations thereof.

In one embodiment, the first portion and the second portion include a clamp configured to engage each other to releasably attach the first portion to the second portion. The first portion and the second portion include a thermoplastic material.

In one embodiment, the first portion is further attached to the second portion with a strap, e.g., a Velcro™ strap or the like.

One embodiment is directed towards a method of using a surgical patch for supporting a secondary medical device during a non-invasive surgical procedure using a radial artery and for providing a desired degree of hemostasis to the radial artery after the non-invasive surgical procedure. The method includes providing a medical device as described herein and locating a radial artery. The method also includes cleaning the area around the located radial artery. The method includes removing a peel away sheet to expose an adhesive of part of the medical device and attaching part of the device to a wrist of the patient such that the cut out region exposes the cleaned located radial artery. A secondary device is supported into or with the anchor portion, clamp and/or other portion of the medical device, e.g., hole of second portion of the device and the secondary resided through a portion of the hole. Next, the non-invasive surgical procedure is completed and the secondary device is removed. The second portion of the device is fully attached to the first portion and/or skin of the patient with the adhesive. Next, the compression bladder is utilized to create hemostasis to stop of minimize bleeding from or near an insertion site of the radial arterial or a previous location of the secondary device.

In one embodiment, the use of the medical device allows for clean sterile field through and after the procedure, thereby reducing complications and infections.

In one embodiment, the medical device is placed in a sterile manner by the clinician at the precise location of the puncture site and securely holds the sheath in place thereby reducing the risk of one or more of infection, local bleeding, and trauma to the artery by not allowing the sheath to move in and out of the puncture site during catheter exchanges. After the procedure, the device is used to provide a predetermined degree of hemostasis of the artery and reduce the risk of hematoma formation by applying pressure at the exact needle entry site and by not allowing the compression system to move out of position during the compression protocol which is a common problem with current compression bands.

One embodiment includes a method of using the medical device for two purposes including supporting and/or securing a secondary device to the medical device and for controlling a patient's bleeding and achieving hemostasis of the radial artery.

In one embodiment, the compression device is applied with a mechanical mechanism.

In one embodiment, the method for compressing a radial artery at an access site of a radial artery of a patient includes providing a radial artery compression device including an inflation device, e.g., pump or syringe, configured to apply pressure to the compression bladder. The medical device includes an anchor mechanism configured to support a secondary device during the non-invasive position. The medical device is attached to the wrist of the patient prior to and/or during the medical procedure, thereby allowing for a continuous sterile field. The compression device has a bladder that can be inflated with a pump to a desired pressure in a continuous or non-continuous manner in order to achieve a desired state of hemostasis.

In one embodiment, the inventor believes the use of the medical device with a compressions device will result in hemostasis in one hour or less, preferably in 30 minutes or less and most preferably in 15 minutes or less. In one aspect hemostasis may be achieved within 10 minutes or less. However, most patients receive anticoagulation at the beginning of the procedure, hemostasis may be delayed and occur in about 1 hour to about 2 hours or even greater in those patients.

Reference will now be made in detail to an embodiment of the present invention, example of which is illustrated in the accompanying drawings.

FIG. 1 illustrates an exemplary top plan view of a medical device according to an embodiment of the invention.

Referring to FIG. 1, the medical device is generally depicted with reference to number 100. The device 100 is in the form of a patch configured to be adhered to a patient. The device 100 is configured to hold at least a portion of a secondary device and also configured as a compression system. The device 100 allows the user to preserve a sterile field in use.

Optionally, the device 100 includes an optional strap 102 configured to be adjustable around the patient's wrist (not shown) and configured to support and hold the device in place. In a preferred embodiment, there is no strap and the device is set forth asa patch device that resides solely on one side of a patient's wrist. The device 100 is positioned such that it fits over an inside portion of the patient's wrist.

The device 100 has a first portion 104 and a second portion 106. The first portion 104 is connected to the second portion 106 with a hinge portion 105, e.g., living hinge portion. The hinge portion 105 hinge may be produced by thinning, reducing and/or perforating an amount of material at the desired bend point. The hinge portion 105 can be formed by molding, cutting, stamping, perforating, and/or thinning a portion of the material at the fold. The second portion 106 includes an anchor portion 108, e.g., a holder, configured to support a portion of the secondary device 109.

The second portion includes a sterile adhesive portion (not shown) on the second surface 107 opposite the first surface 111. The sterile adhesive portion is configured to adhere the entire surface of the second portion 106 to the skin of a patient in a releasable manner.

In one embodiment, the anchor mechanism 108 is sized and shaped to accept a portion of the secondary device, e.g., concave shape or other type shape. That is, the anchor mechanism 108 can have a portion configured, e.g., a recessed portion, to receive a portion of the secondary device 109. In another embodiment, the anchor mechanism 108 can also include securing strap or material configured (not shown) to go over a portion of the secondary device and releasably couple a portion of the secondary device to the second portion 106.

The first portion 104 includes a compression mechanism 110. In this embodiment, the compression mechanism 110 includes an expandable member 110 configured to expand and apply pressure to a wound. The expandable member 110 can include a balloon, capable of being inflated or deflated. In one embodiment, the expandable member 110 includes an inflation tube or port 112 through which air or fluid can be passed to inflate the expandable member 110.

In operation, when the secondary medical device, e.g., sheath and catheters, is removed from the radial artery it naturally bleeds. In order to assist with minimizing and stopping the bleeding, pressure is applied to the area that is bleeding. In one embodiment, the pressure can be applied by moving the first portion 104 over the second portion 106 and expanding the expandable member 110. For example, in one embodiment, the expandable member 110 is a balloon and pressure is added with a compressible or non-compressible fluid. The pressure aids with hemostasis of the wound. Without the pressure hemostasis would occur more slowly.

The first portion 104 also includes an adhesive portion 116 configured to attach to a patient's skin. The adhesive portion 116 can be a peel away release adhesive material that is sterile. The adhesive portion 116 also includes a second adhesive portion 118 configured to secure it to a surface of the second portion 106 in a non-releasable manner. The second adhesive 118 material is the same as the first or stronger material. Both materials are configured to be sterile.

The second portion 106 includes a cutout region 114 in a partial half circle geometry. The cutout 114 gives access to a patient's skin and the puncture site where the secondary device will be inserted into a patient's artery or vein. The cutout 114 can be any geometry, e.g., circle, square, triangle, diamond, combinations of the same and the like.

Optionally and/or alternatively, the first portion 104 and/or the second portion 106 can also include a secondary attachment mechanism or mechanisms (not shown) configured to allow the first portion to releasably or non-releasably attach to the second portion. The secondary attachment mechanism can include snaps, Velcro, adhesive, buckles, fasteners, combinations of the same and the like.

Figure 2:
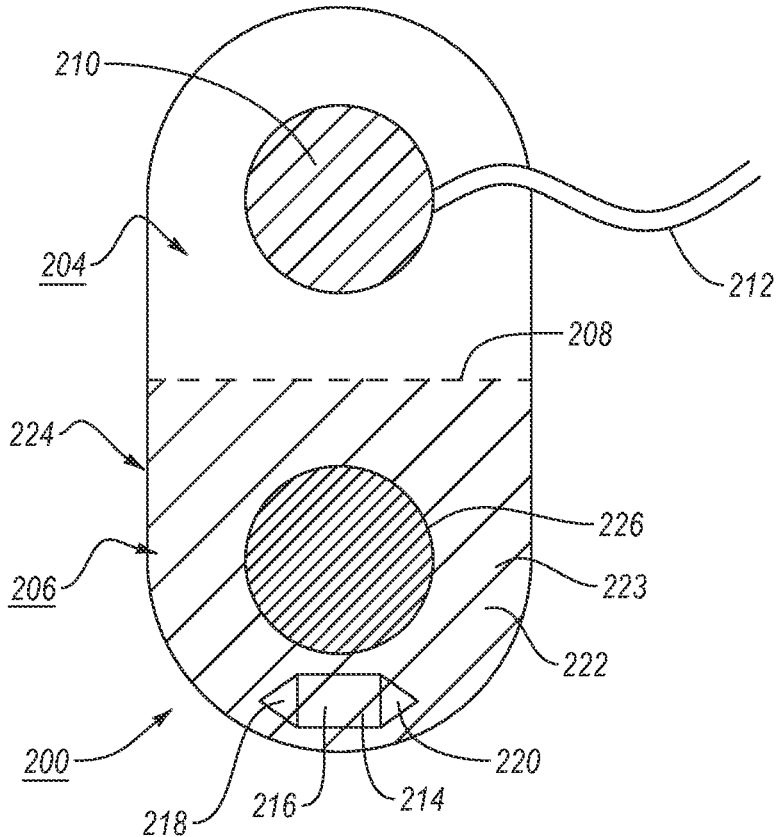
FIG. 2 illustrates an exemplary top plan view of a medical device according to another embodiment of the invention.

FIG. 2 illustrates an exemplary top plan view of a medical device according to another embodiment of the invention.

Referring to FIG. 2, the medical device is generally depicted with reference to number 200. The device 200 is in the form of a patch configured to be adhered to a patient. The device 200 is configured to hold at least a portion of a secondary device and also configured as a compression system. The device 200 allows the user to preserve a sterile field in use. In this embodiment, there is no strap that goes around a wrist of a patient, hand of a user or other anatomy of the user.

The device 200 has a first portion 204 and a second portion 206. The first portion 204 is coupled to the second portion 206 with a hinge portion 208, e.g., a fold portion living hinge as described herein.

The first portion 204 includes a compression mechanism 210 as described herein with an inflation tube or port 212 through which air or fluid can be passed to inflate the expandable member.

The second portion 206 includes an anchor portion 214, e.g., holder, configured to support a portion of the secondary device (not shown). In this embodiment, the anchor portion 214 includes a recessed portion 216 configured to receive a portion of the secondary device. The recessed portion 216 is positioned between the first raised portion 218 and the second raised portion 220. The anchor portion 214 may include any anchor portion described herein.

The second portion 206 includes a first surface 222 and a second opposite surface 224. The first surface includes a sterile adhesive portion 223 configured to adhere to the first portion 204 in a non-releasable manner. The second surface 224 includes a second sterile adhesive portion (not shown) configured to attach to the skin of a patient in a releasable manner.

The second portion 206 includes a cutout region 226 with a circle geometry. The cutout 226 gives access to a patient's skin and the puncture site where the secondary device is going to be inserted into a patient's artery or vein. The cutout 226 can be any geometry, e.g., circle, square, triangle, diamond, combinations of the same and the like.

Optionally and/or alternatively, the first portion 204 and/ or the second portion 206 can also include a secondary attachment mechanism or mechanisms (not shown) configured to allow the first portion to releasably or non-releasably attach to the second portion. The secondary attachment mechanism can include snaps, Velcro, adhesive, buckles, fasteners, combinations of the same and the like.

Figure 3:
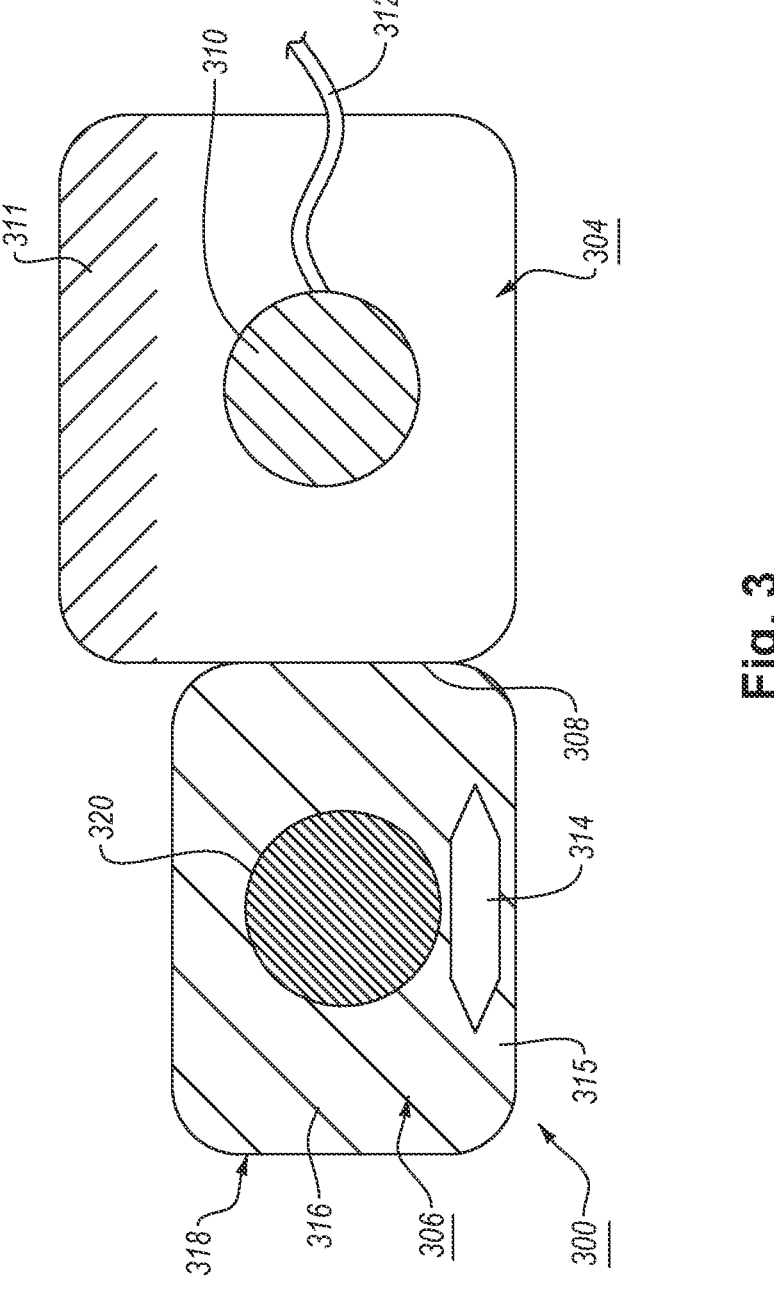
FIG. 3 illustrates an exemplary top plan view of a medical device according to another embodiment of the invention.

FIG. 3 illustrates an exemplary top plan view of a medical device according to another embodiment of the invention.

Referring to FIG. 3, the medical device is generally depicted with reference to number 300. The device 300 is in the form of a patch configured to be adhered to a patient. The device 300 is configured to hold at least a portion of a secondary device (not shown) and also configured as a compression system. The device 300 allows the user to preserve a sterile field in use. In this embodiment, there is no strap that goes around a wrist of a patient, hand of a user or other anatomy of the user.

The device 300 has a first portion 304 and a second portion 306. The first portion 304 is coupled to the second portion 306 with a hinge portion 308, e.g., fold portion living hinge as described herein.

The first portion 304 includes a compression mechanism 310 as described herein with an inflation tube or port 312 through which air or fluid can be passed to inflate the expandable member. The first portion 304 includes an adhesive material 311 configured to adhere to a portion a patient's skin.

The second portion 306 includes an anchor portion 314, e.g., holder, configured to support a portion of the secondary device (not shown). In this embodiment, the anchor portion 314 includes a raised portion configured to receive a portion of the secondary device. The anchor portion 314 may include any anchor portion described herein.

The second portion 306 includes a first surface 316 and a second opposite surface 318. The first surface 316 includes a sterile adhesive portion 315 configured to adhere to the first portion 304 in a non-releasable manner. The second surface 318 includes a second sterile adhesive portion (not shown) configured to attach to the skin of a patient in a releasable manner.

The second portion 306 includes a cutout region 320 with a circle geometry. The cutout 320 gives access to a patient's skin and the puncture site where the secondary device is going to be inserted into a patient's artery or vein. The cutout 320 can be any geometry, e.g., circle, square, triangle, diamond, combinations of the same and the like.

Optionally and/or alternatively, the first portion 304 and/ or the second portion 306 can also include a secondary attachment mechanism or mechanisms (not shown) configured to allow the first portion to releasably or non-releasably attach to the second portion. The secondary attachment mechanism can include snaps, Velcro, adhesive, buckles, fasteners, combinations of the same and the like.

Figure 4:
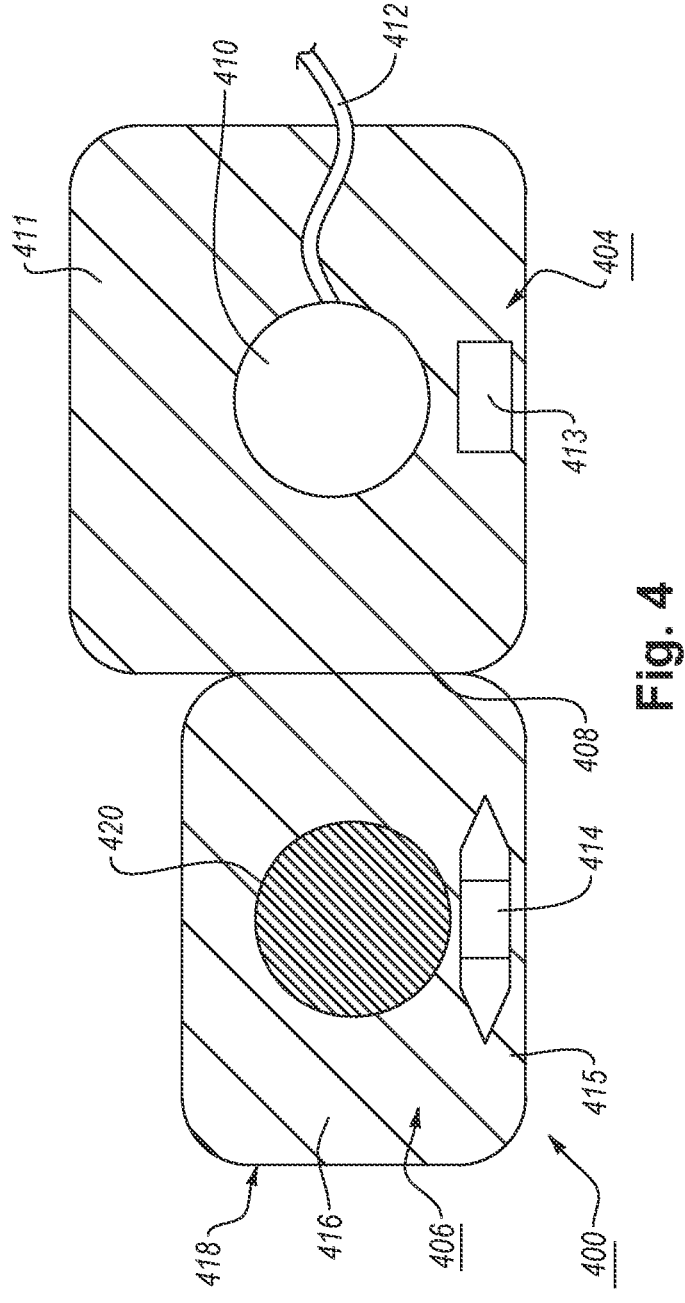
FIG. 4 illustrates an exemplary top plan view of a medical device according to another embodiment of the invention.

FIG. 4 illustrates an exemplary top plan view of a medical device according to another embodiment of the invention.

Referring to FIG. 4, the medical device is generally depicted with reference to number 400. The device 400 is in the form of a patch configured to be adhered to a patient. The device 400 is configured to hold at least a portion of a secondary device (not shown) and also configured as a compression system. The device 400 allows the user to preserve a sterile field in use. In this embodiment, there is no strap that goes around a wrist of user, hand of a user or other anatomy of the user.

The device 400 has a first portion 404 and a second portion 406. The first portion 404 is coupled to the second portion 406 with a hinge portion 408, e.g., fold portion living hinge as described herein. The first portion 404 is sized smaller than the second portion 406.

The first portion 404 includes a compression mechanism 410 as described herein with an inflation tube or port 412 through which air or fluid can be passed to inflate the expandable member. The first portion 404 includes an adhesive material 411 configured to adhere to a portion of a patient's skin and a portion of the second portion 406.

The second portion 406 includes an anchor portion 414, e.g., holder, configured to support a portion of the secondary device (not shown). In this embodiment, the anchor portion 414 includes a raised portion configured to receive a portion of the secondary device. The anchor portion 414 may include any anchor portion described herein. Moreover, the anchor portion is configured to work with anchor 413 on the first portion.

The second portion 406 includes a first surface 416 and a second opposite surface 418. The first surface 416 includes a sterile adhesive portion 415 configured to adhere to the first portion 404 in a non-releasable manner. The second surface 418 includes a second sterile adhesive portion (not shown) configured to attach to the skin of a patient in a releasable manner.

The second portion 406 includes a cutout region 420 with a circle geometry. The cutout 420 gives access to a patient's skin and the puncture site where the secondary device is going to be inserted into a patient's artery or vein. The cutout 420 can be any geometry, e.g., circle, square, triangle, diamond, combinations of the same and the like.

Optionally and/or alternatively, the first portion 404 and/ or the second portion 406 can also include a secondary attachment mechanism or mechanisms (not shown) configured to allow the first portion to releasably or non-releasably attach to the second portion. The secondary attachment mechanism can include snaps, Velcro, adhesive, buckles, fasteners, combinations of the same and the like.

Figure 5:
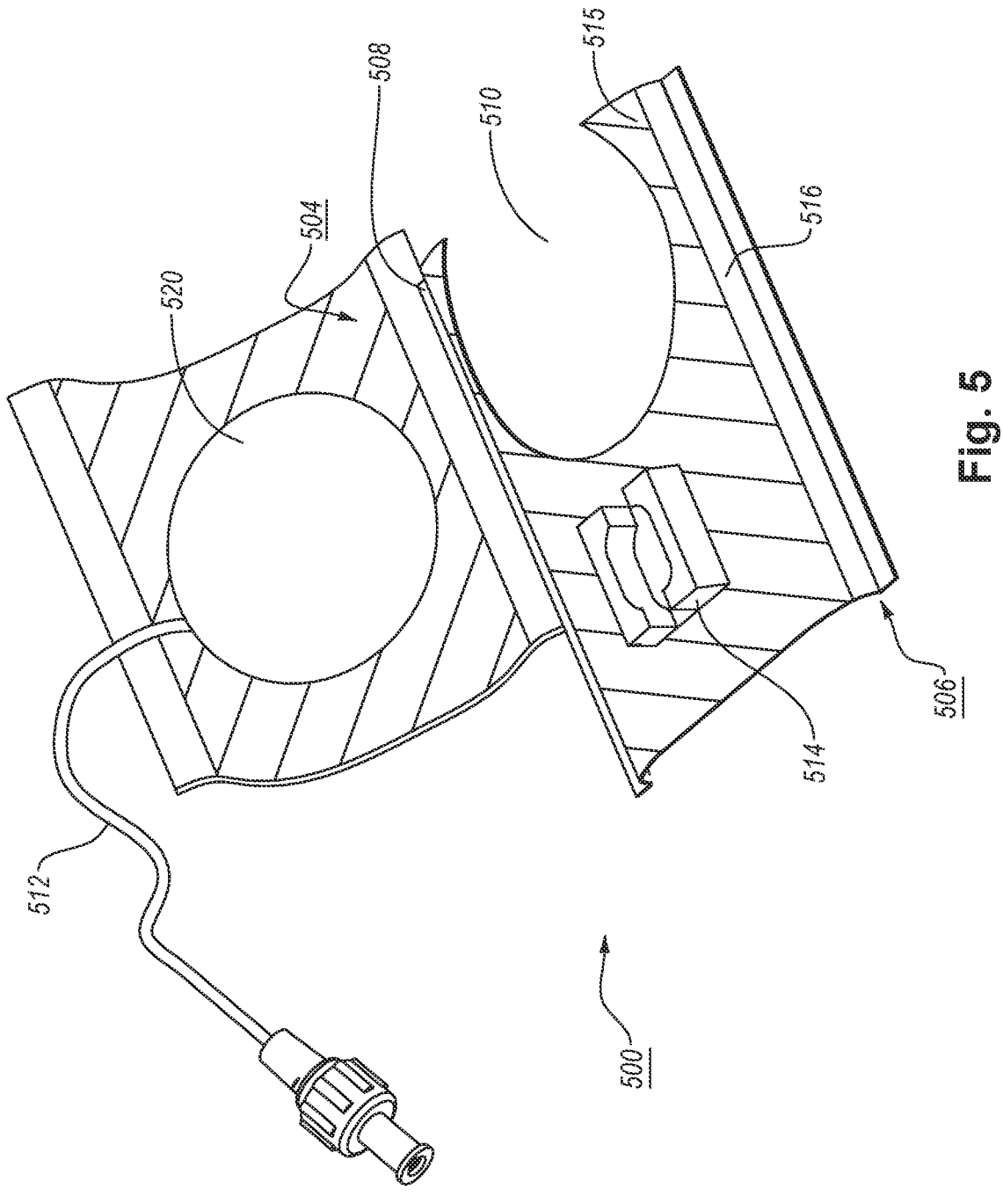
FIG. 5 illustrates an exemplary top plan view of a medical device according to another embodiment of the invention.
Figure 6:
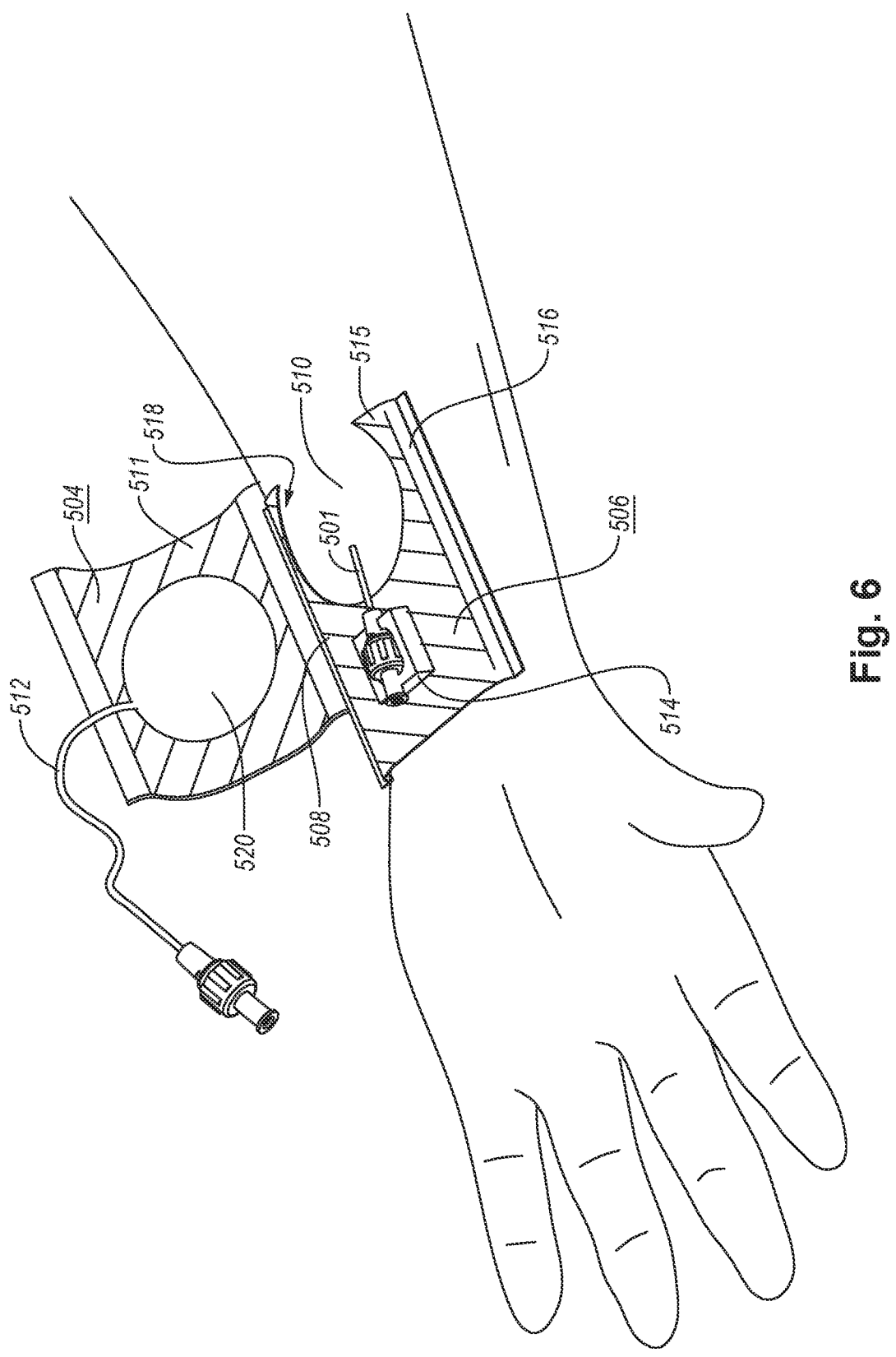
FIG. 6 illustrates an exemplary top plan view of a medical device of FIG. 5 on a patient.

FIG. 5 illustrates an exemplary top plan view of a medical device according to another embodiment of the invention. FIG. 6 illustrates an exemplary top plan view of a medical device of FIG. 5 on a patient.

Referring to FIGS. 5-6, the medical device is generally depicted with reference to number 500. The device 500 is in the form of a patch configured to be adhered to a patient's wrist. The device 500 is configured to hold at least a portion of a secondary device (not shown) and also configured as a compression system. The device 500 allows the user to preserve a sterile field in use. In this embodiment, there is no strap that goes around a wrist of user, hand of a user or other anatomy of the patient.

The device 500 has a first portion 504 and a second portion 506. The first portion 504 is coupled to the second portion 506 with a hinge portion 508, e.g., fold portion living hinge as described herein. The first portion 504 is offset from the second portion 506.

The first portion 504 includes a compression mechanism 520 as described herein with an inflation tube or port 512 through which air or fluid can be passed to inflate the expandable member. The first portion 504 includes an adhesive material 511 configured to adhere to a portion of a patient's skin and a portion of the second portion 506.

The second portion 506 includes an anchor portion 514, e.g., holder, configured to support a portion of the secondary device (not shown). In this embodiment, the anchor portion 514 includes a raised portion configured to receive a portion of the secondary device 501. The anchor portion 514 may include any type of anchor portion described herein. Moreover, the anchor portion is configured to work with anchor 514 on the second portion 506.

The second portion 506 includes a first surface 516 and a second opposite surface 518. The first surface 516 includes a sterile adhesive portion 515 configured to adhere to the first portion 504 in a non-releasable manner. The second surface 518 includes a second sterile adhesive portion (not shown) configured to adhere to the skin of a patient in a releasable manner.

The second portion 506 includes a cutout region 510 with a half circle geometry. The cutout 510 gives access to a patient's skin and the puncture site where the secondary device is going to be inserted into a patient's artery or vein. The cutout 510 can be any geometry, e.g., circle, square, triangle, diamond, combinations of the same and the like.

Optionally and/or alternatively, the first portion 504 and/or the second portion 506 can also include a secondary attachment mechanism or mechanisms (not shown) configured to allow the first portion to releasably or non-releasably attach to the second portion. The secondary attachment mechanism can include snaps, Velcro, adhesive, buckles, fasteners, combinations of the same and the like.

FIGS. 7A-7D illustrate an exemplary top plan view of FIG. 5 in different use orientations.

Figures 7A, 7B:
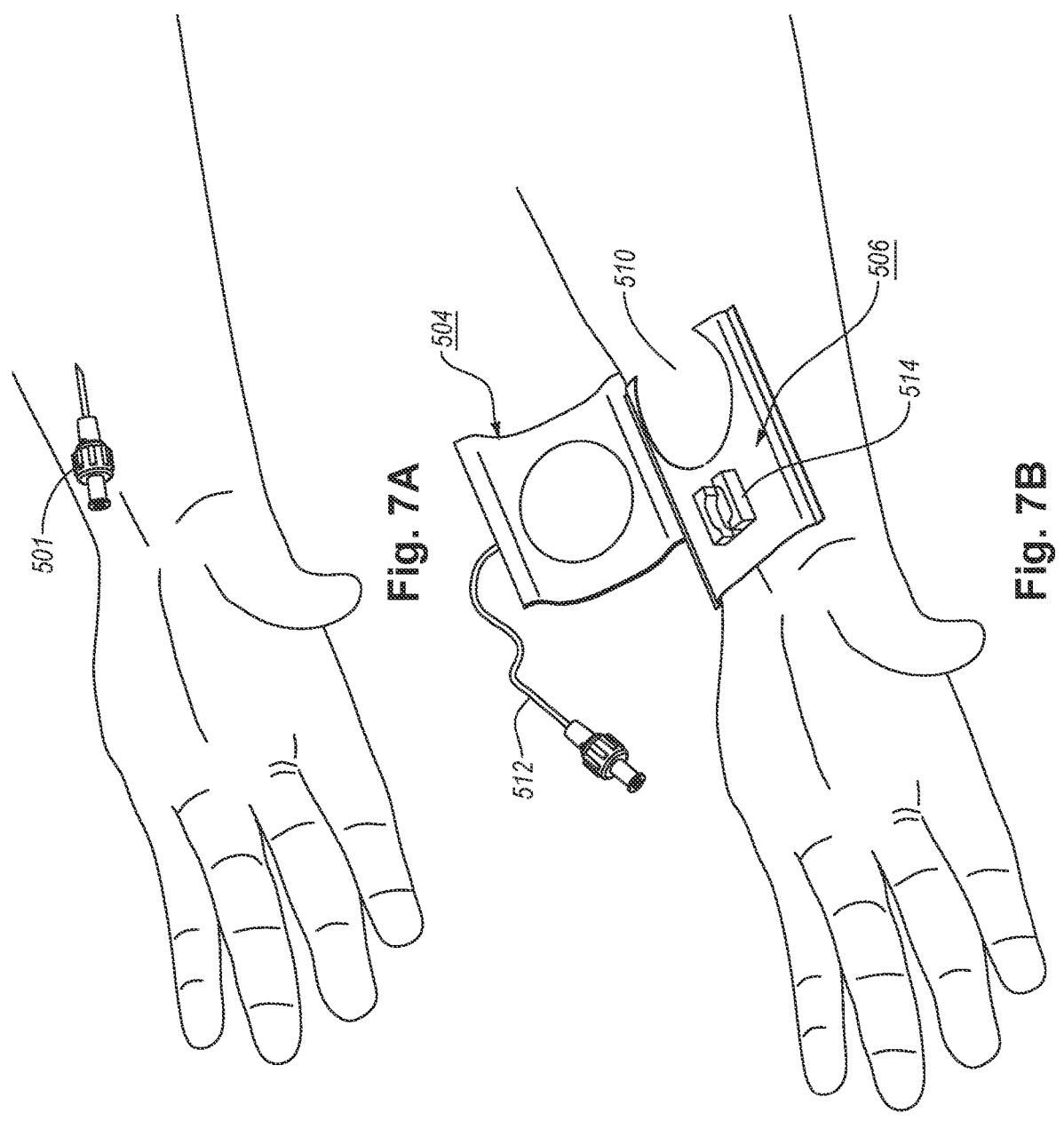
FIGS. 7A-7D illustrate an exemplary top plan view of a FIG. 5 in different use orientations.
Figures 7C, 7D:
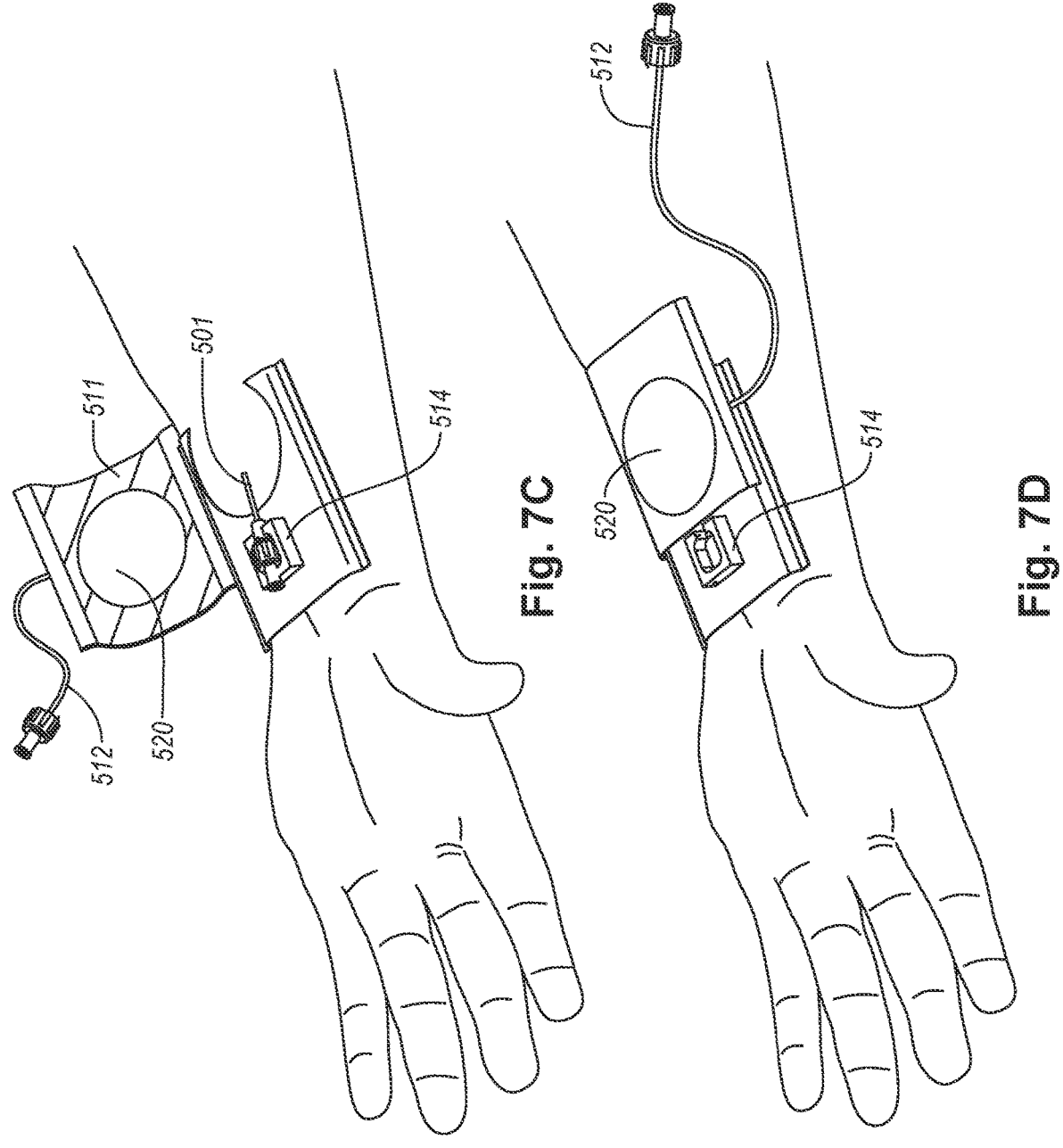

Referring to FIGS. 7A-7D, in use a secondary device 501 is inserted into a sterile zone of a patient's situs (FIG. 7A). The device 500 is adhered with the second portion 506 to and configured to support a portion of the secondary device 501 with an anchor 514 as shown in FIG. 7B. The medical procedure is completed on the patient and the secondary device 501 is removed as shown in FIG. 7C. The first portion 504 is folded and adhered to the patient's arm and second portion 506. At that point, the compression device 520 is inflated via the inflation port 512 to provide pressure to the site of bleeding as shown in FIG. 7D. Other embodiments of the device may feature releasable attachment means instead of the adhesive with releasable liner, such as, but not limited to hook and loop fasteners.

Figure 8:
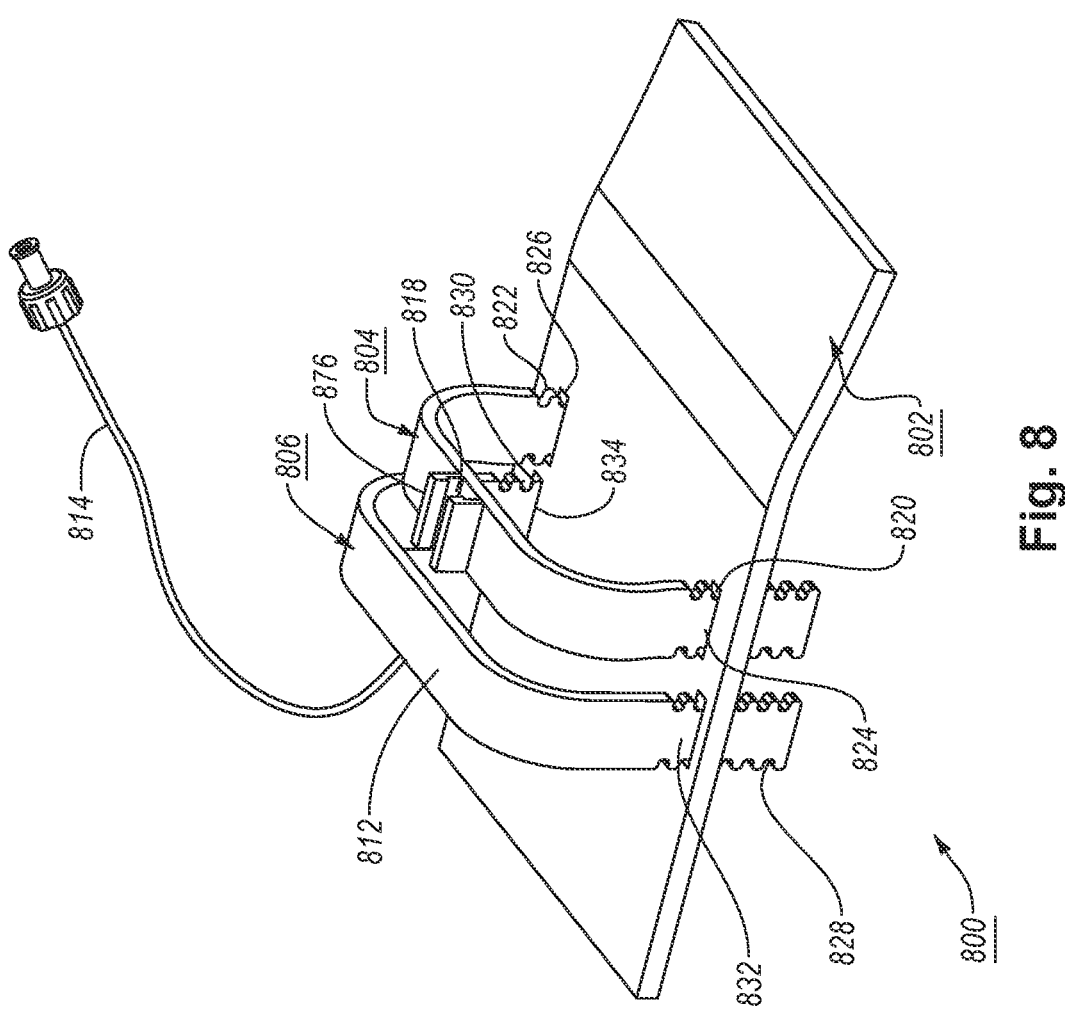
FIG. 8 illustrates an exemplary top plan view of a medical device according to another embodiment of the invention.

FIG. 8 illustrates an exemplary top plan view of a medical device according to another embodiment of the invention.

Figure 9:
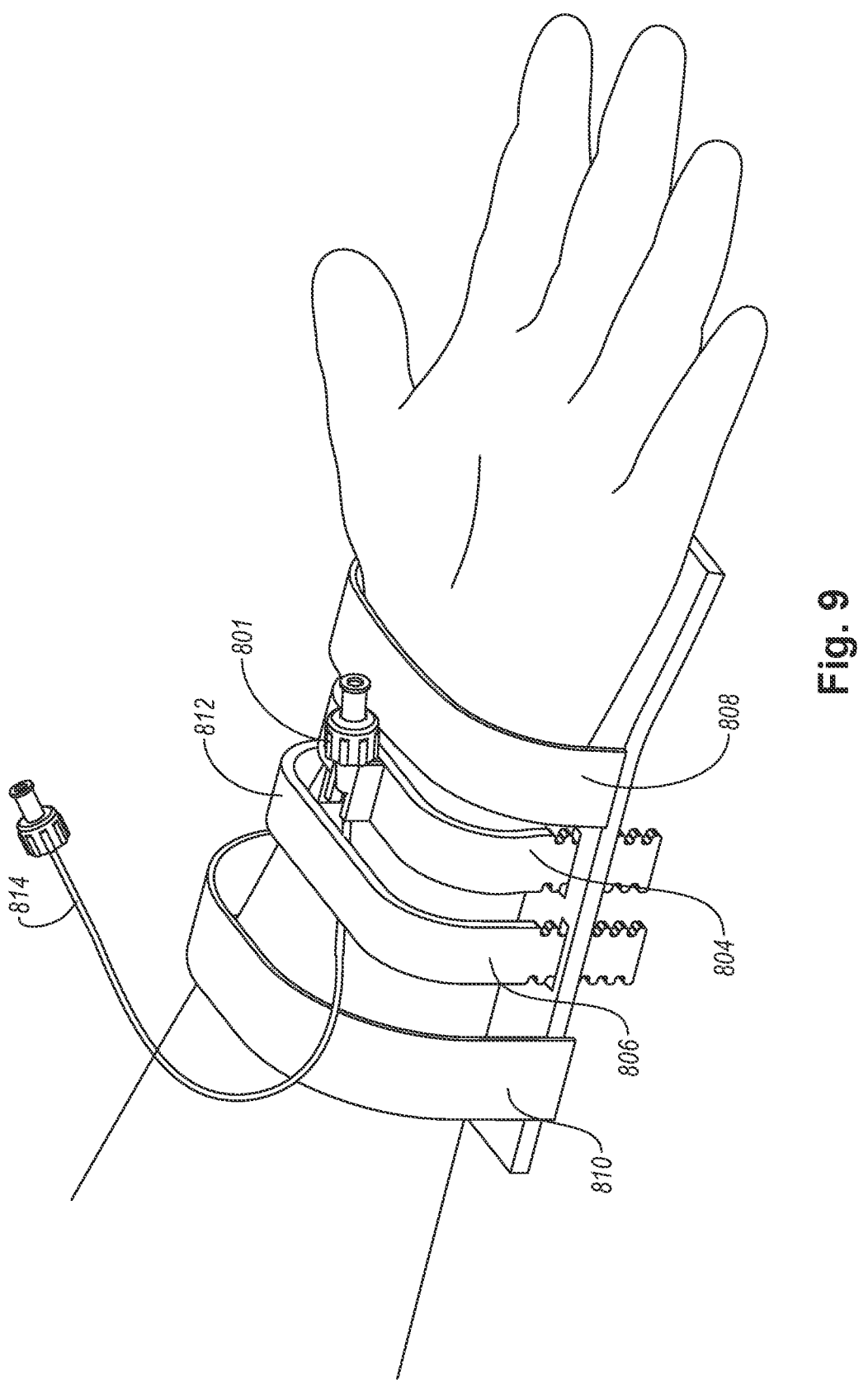
FIG. 9 illustrates an exemplary top plan view of the medical device of FIG. 8.

FIG. 9 illustrates an exemplary top plan view of the medical device of FIG. 8 on a patient.

Referring to FIGS. 8-9, the medical device is generally depicted with reference to number 800. The device 800 includes a base portion 802, a first portion 804 and a second portion 806. The device 800 is configured to hold at least a portion of a secondary device 801 and also configured as a compression system. The device 800 allows the user to preserve a sterile field in use.

Optionally and/or alternatively, the device 800 includes a first strap 808 and a second strap 810. The first strap 808 and the second trap 810 are adjustable. The first strap 808 and the second strap 810 are made from one or more of an expandable material, clothing material, thermoplastic material, plastic material, polymer material, and combinations of the same.

The first portion 804 includes an anchor portion 816, e.g., holder, configured to support a portion of the secondary device 801. In this embodiment, the anchor portion 816 includes a raised portion with a recessed slot 818 to receive a portion of the secondary device 801. The anchor portion 816 and may include any anchor portion described herein. The first portion 804 is configured to be releasably attached to the base 802 at different orientations. The first portion 804 includes a first end and a second end. The first end includes a region with a plurality of cutout portions 820 and the second end includes a region with a plurality of cutout portions 822. The cutout portions 820 are configured to be releasably attached to the base 802 through a slot 824. The cutout portions 822 are configured to be releasably attached to the base 802 through a slot 826.

The second portion 806 is configured to be releasably attached to the base 802 at different orientations. The second portion 806 includes a first end and a second end. The first end includes a region with a plurality of cutout portions 828 and the second end includes a region with a plurality of cutout portions 830. The cutout portions 828 are configured to be releasably attached to the base 802 through a slot 832. The cutout portions 830 are configured to be releasably attached to the base 802 through a slot 834.

The first portion 804 and the second portion 806 are constructed from one or more of a thermoplastic material, a plastic material, a polymer material and combinations thereof. The material is flexible.

The second portion 806 includes a compression mechanism 812 as described herein with an inflation tube or port 814 through which air or fluid can be passed to inflate the expandable member.

FIGS. 10A-10D illustrates an exemplary top plan view of the device of FIG. 8 in different use orientations.

Figures 10A, 10B:
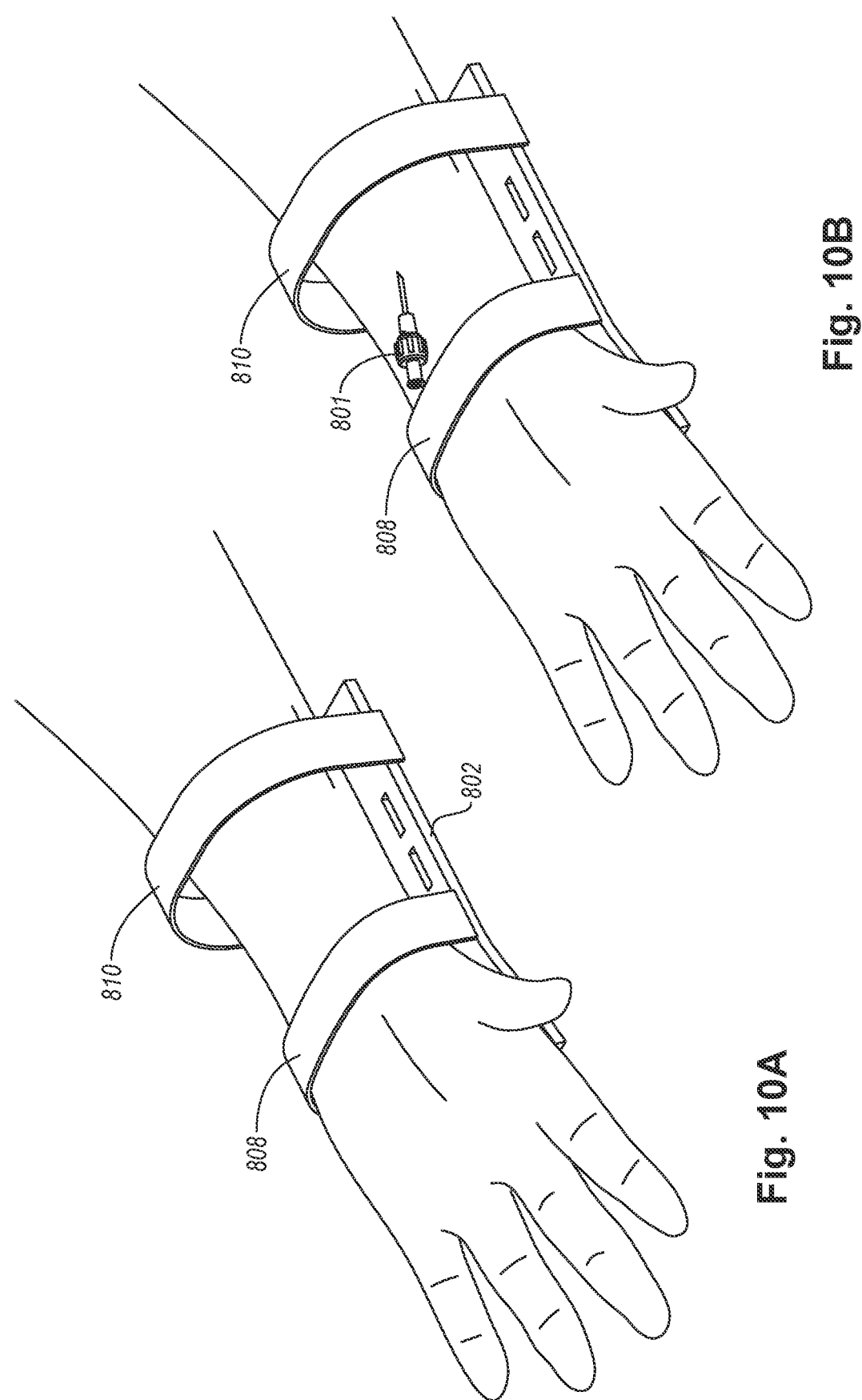
FIGS. 10A-10D illustrate an exemplary top plan view of the device of FIG. 8 in different use orientations.
Figures 10C, 10D:
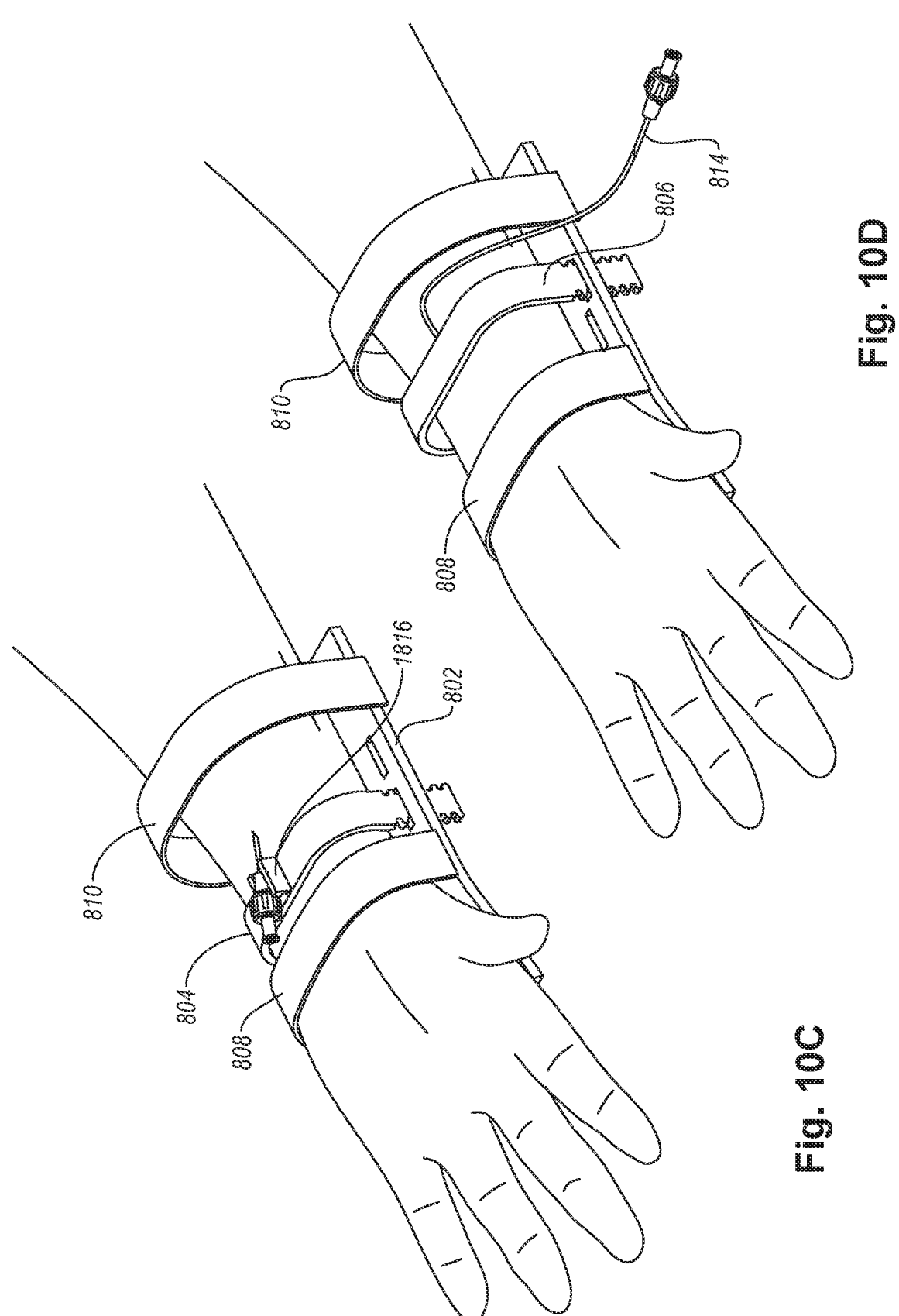

Referring to FIGS. 10A-10D, in use the medical device 800 is arranged over a patient's wrist with the first strap 808 and the second strap 810 shown in FIG. 10A. The secondary device 801 is inserted into a sterile zone of a patient's situs (FIG. 10A). The physician then proceeds with the surgical procedure by making an incision and inserting the second device 801, e.g., a sheath into the patient's circulatory system, the radial artery in this example. Next, the first portion 804 is releasably attached to the base 802 as shown in FIG. 10C. When not being physically manipulated, the free end of the sheath 801 is placed into the anchor 816 to be held in place during the rest of the surgical procedure (FIG. 10C). When the procedure is completed and the secondary device 801, e.g., sheath, is removed from the patient, the releasable liner is removed from the surface of the device. Optionally, the first portion 804 is removed.

The second portion 806 is attached to the base 802 as shown in FIG. 10D. The compression device 812 is inflated via the inflation port 814 to provide pressure to the site of bleeding.

Figures 11, 12:
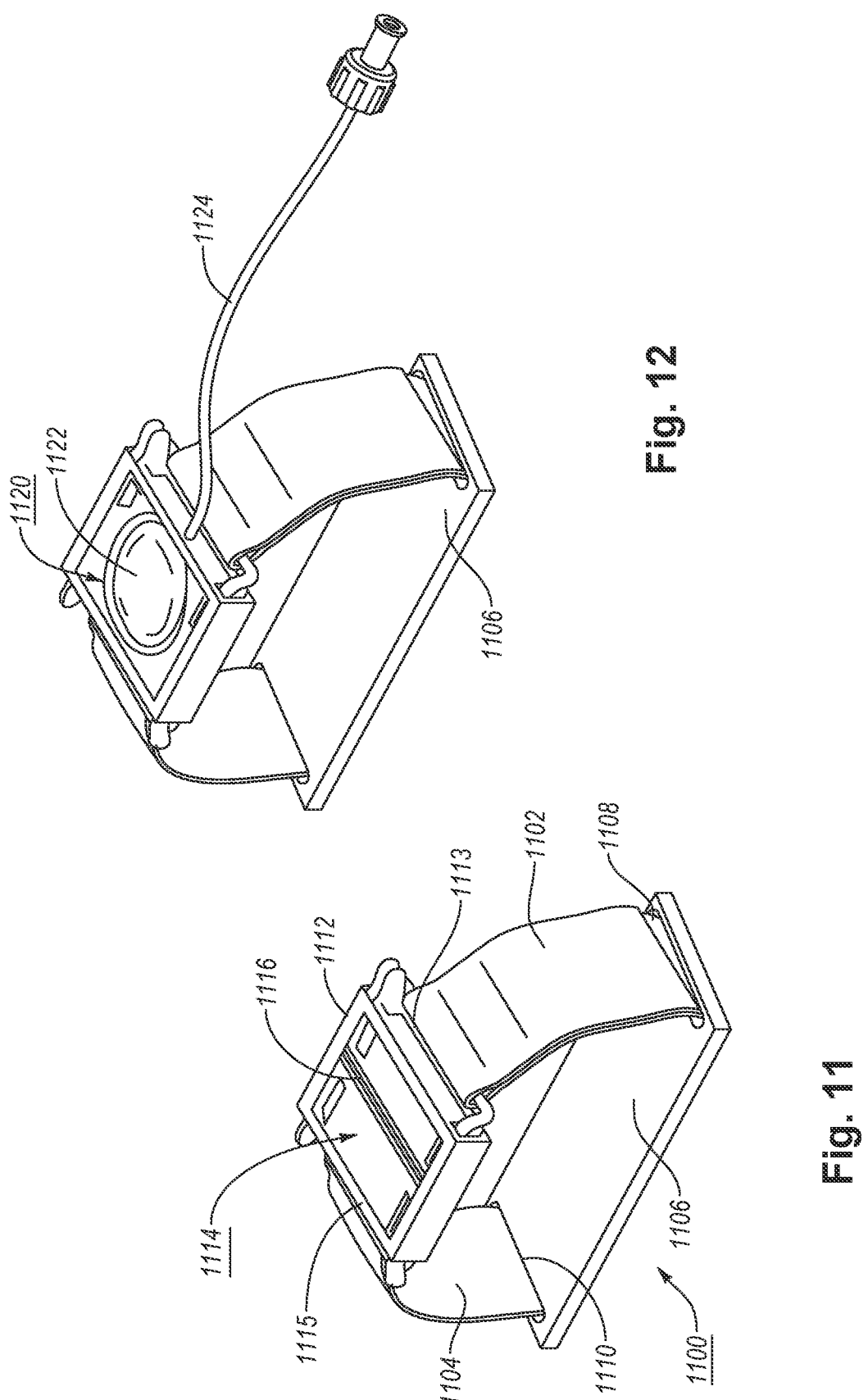
FIG. 11 illustrates an exemplary top plan view of a medical device according to another embodiment of the invention.
FIG. 12 illustrates an exemplary top plan view of a medical device of FIG. 11 on a patient.

FIG. 11 illustrates an exemplary top plan view of a medical device according to another embodiment of the invention. FIG. 12 illustrates an exemplary top plan view of a medical device of FIG. 11 on a patient.

Referring to FIGS. 11-12, the medical device is generally depicted with reference to number 1100. The device 1100 is configured to hold at least a portion of a secondary device (not shown) and also configured as a compression system. The device 1100 allows the user to preserve a sterile field in use. In this embodiment, there is a first strap 1102 and a second strap 1104 coupled to a base 1106. Optionally, the is only one strap and no base. In this embodiment, the first strap 1102 is adjustable and configured to be inserted into a slot 1108 of the base, the second strap 1104 is adjustable and configured to be inserted into a slot 1110. The first strap 1102, second strap 1104 and the base 1106 go around a wrist of user, hand of a user or other anatomy of the patient.

The device 1100 has a first portion 1114 releasably arranged within an interior of a frame 1112. The frame 1112 has four sides and is configured to releasably secure the first portion 1114 with a holding mechanism. The frame 1112 includes a first region 1113, e.g., slot, to secure the first strap 1102 and a second region 1115, e.g., slot, to secure the second strap 1104. The holding mechanism includes a snap system or other type of securing system, e.g., tongue and grove system or the like as may be known in the art. The first portion 1114 includes an anchor portion 1116 configured to receive and releasably secure a secondary device (not shown).

The device 1110 further includes a second portion 1120 that includes a compression mechanism 1122 as described herein with an inflation tube or port 1124 through which air or fluid can be passed to inflate an expandable member. The frame 1112 has four sides and is configured to releasably secure the second portion 1120 with a holding mechanism. The holding mechanism includes a snap system or other type of securing system, e.g., tongue and groove system or the like as may be known in the art.

FIGS. 13A-13D illustrate an exemplary top plan view of the device of FIGS. 11-12 in different use orientations.

Figures 13A, 13B:
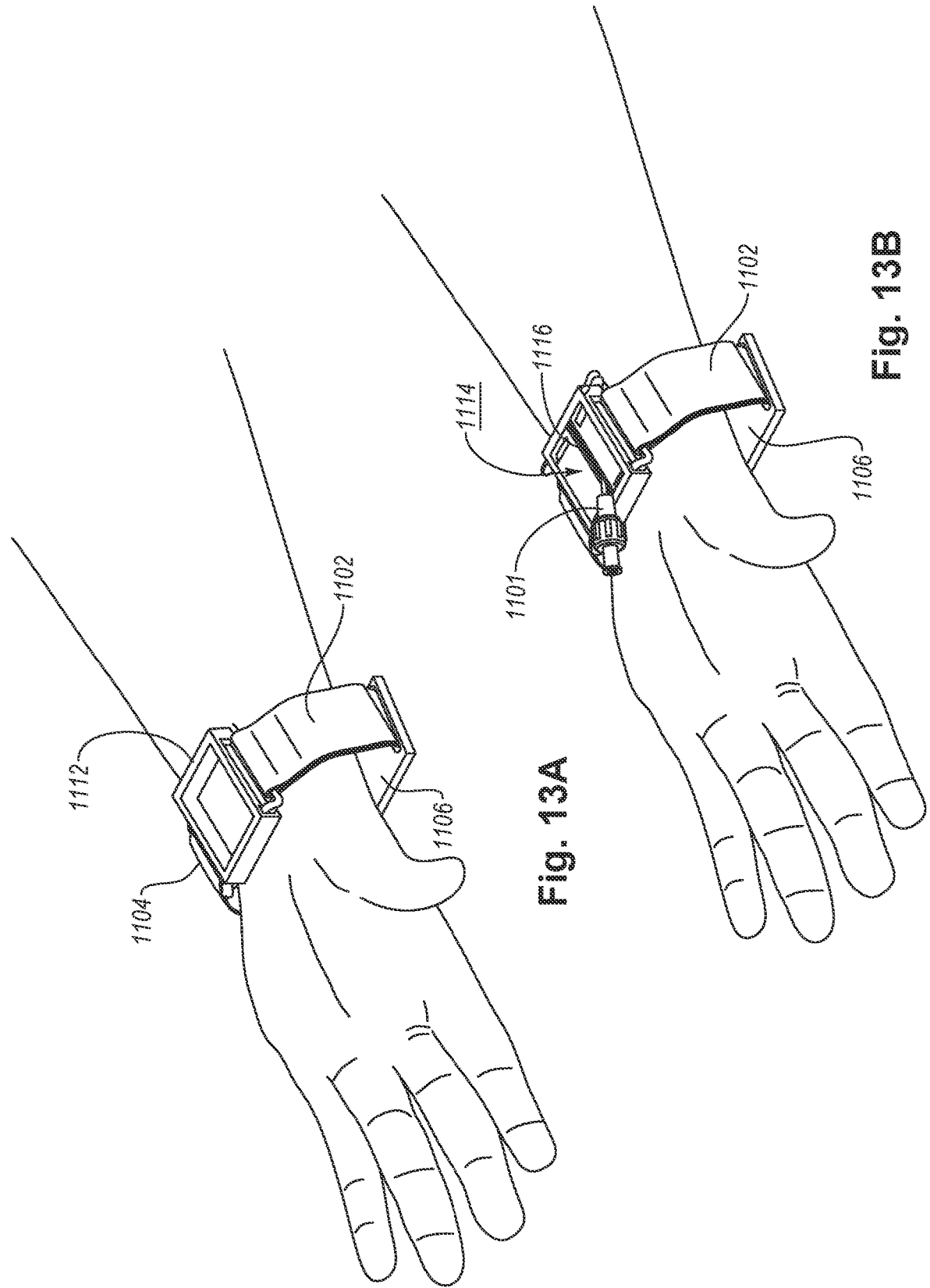
FIGS. 13A-13D illustrate an exemplary top plan view of a FIG. 5 in different use orientations.

Referring to FIGS. 13A-13D, the device 1100 is configured to hold at least a portion of a secondary device 1101 and is also configured as a compression system. The device 1100 allows the user to preserve a sterile field in use. The first strap 1102 and a second strap 1104 are coupled to a base 1106 around the wrist of a patient as shown in FIG. 13A and in use a secondary device 1101 is inserted into a sterile zone of a patient's situs. Next, the first portion 1114 is releasably attached to the frame 1112 as shown in FIG. 13B and the secondary device 1101 is secured to the anchor portion 1116. The secondary device 1101 is held in place during the rest of the surgical procedure (FIG. 13B). Then the procedure is completed and the sheath 1301 is removed from the patient, and the releasable liner is removed from the surface of the device. The first portion 1114 is now removed.

Figures 13C, 13D:
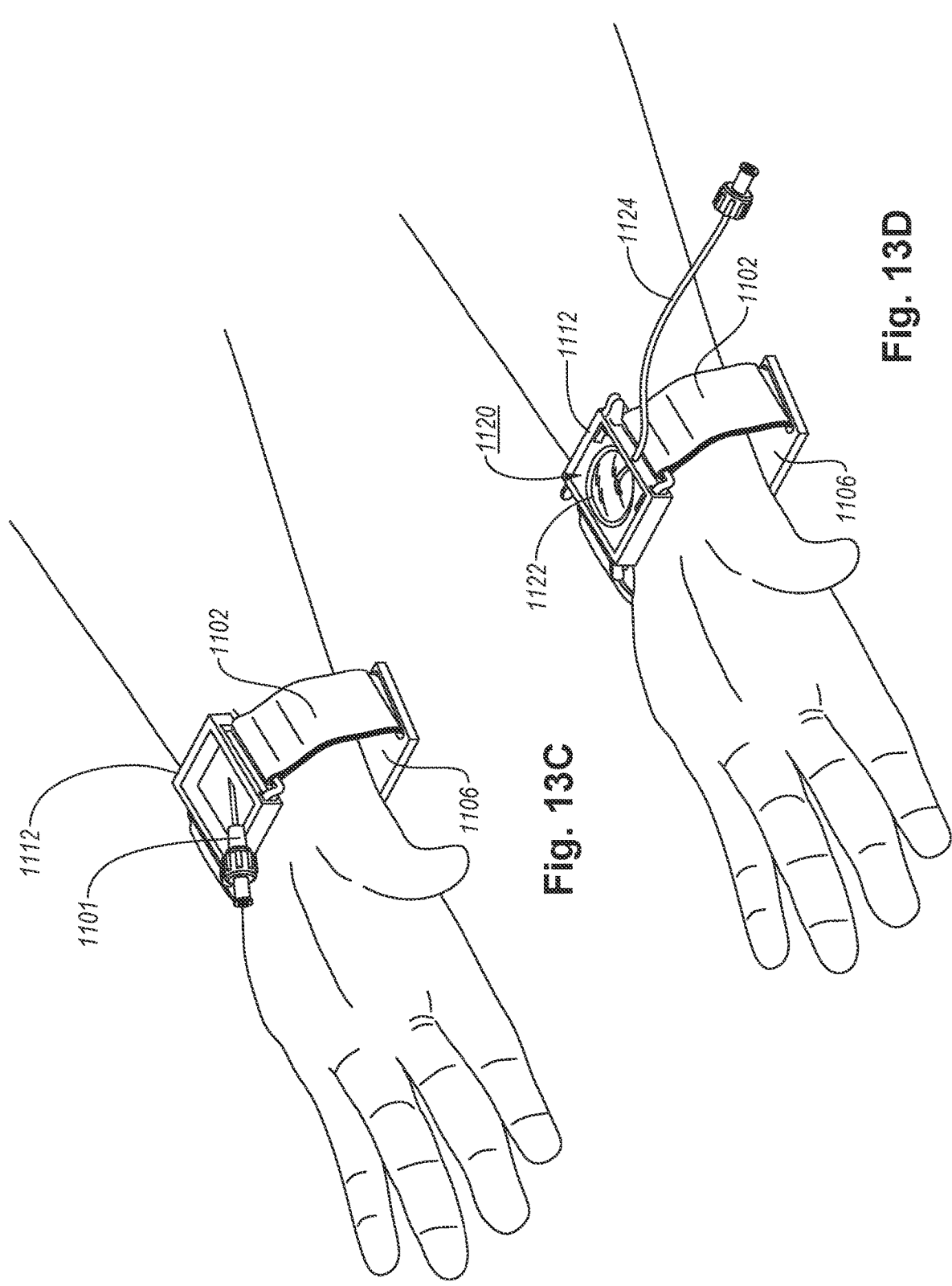

The second portion 1120 is attached to the device 1100 as shown in FIG. 13D. The compression device 1122 is inflated via the inflation port 1124 to provide pressure to the site of bleeding.

Figure 14:
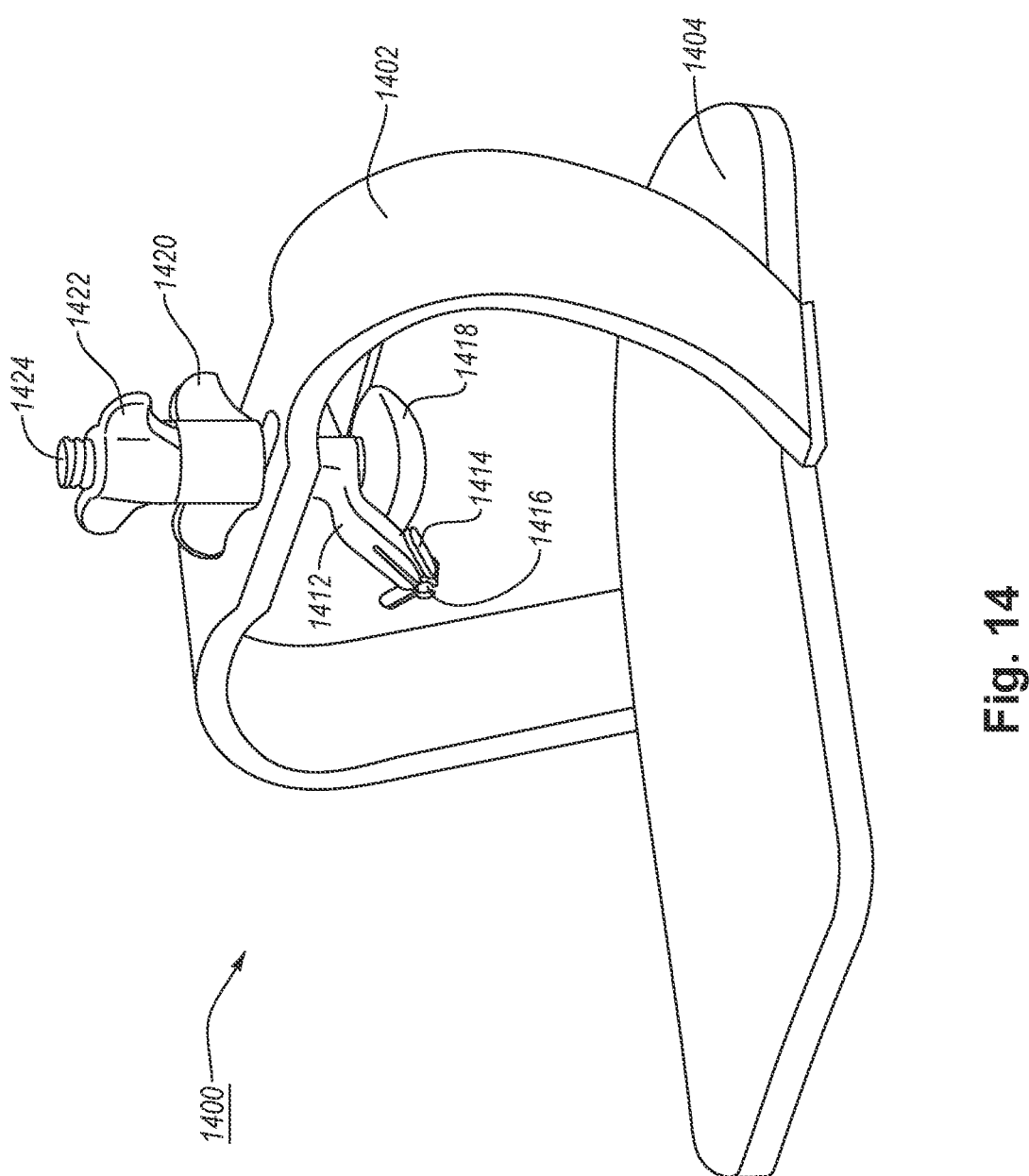
FIG. 14 illustrates an exemplary top plan view of a medical device according to another embodiment of the invention.
Figure 15:
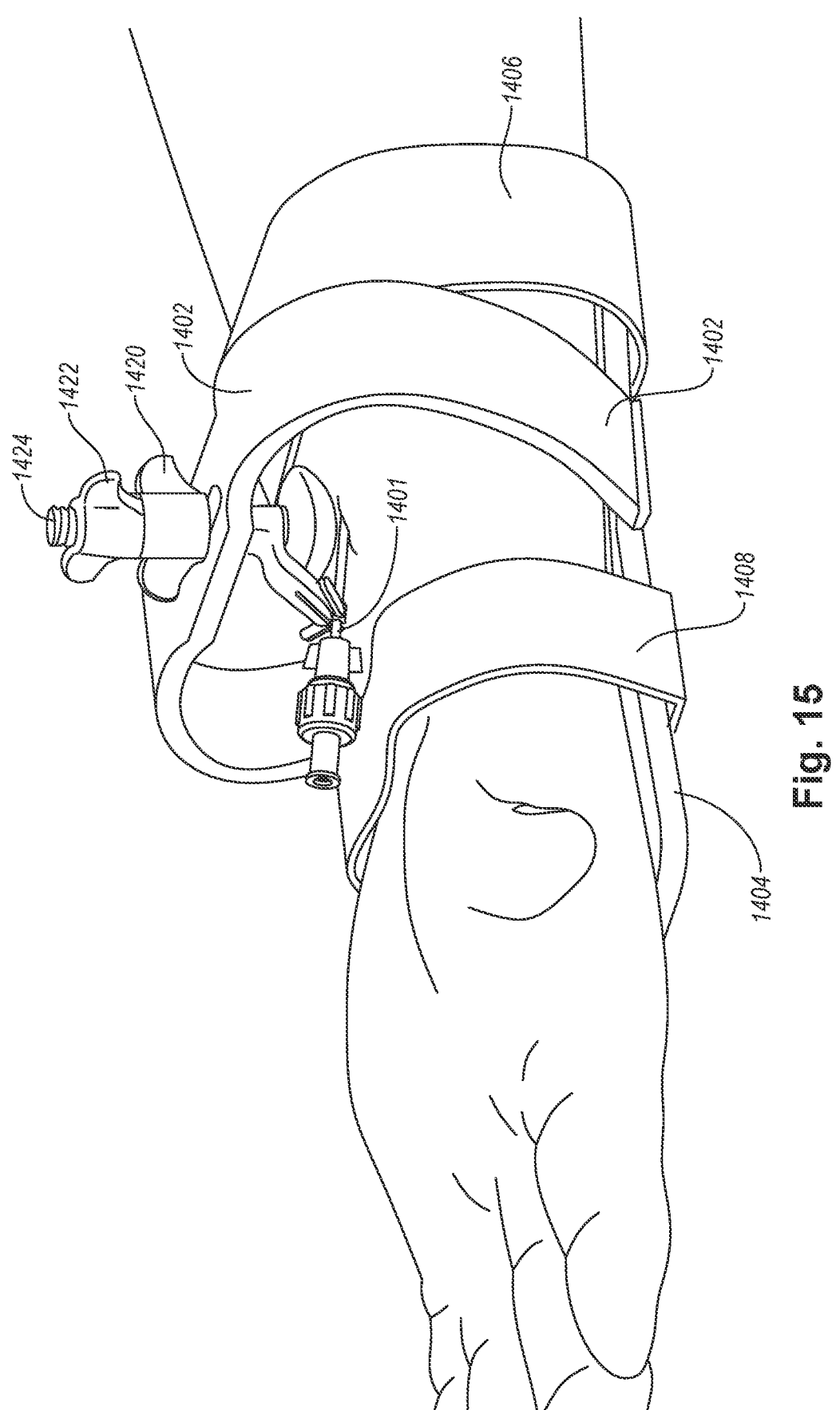
FIG. 15 illustrates an exemplary top plan view of a medical device of FIG. 14 on a patient.

FIG. 14 illustrates an exemplary top plan view of a medical device according to another embodiment of the invention. FIG. 15 illustrates an exemplary top plan view of a medical device of FIG. 14 on a patient.

Referring to FIGS. 14-15, the medical device is generally depicted with reference to number 1400. The device 1400 includes a strap portion 1402 attached to a base portion 1404. The base portion 1404 extends along an axis configured to extend along a length of an arm. The strap portion 1402 can be adjustable from a first circumference to a second circumference.

Optionally and/or alternatively, the device 1400 includes a first strap 1406 and a second strap 1408. The first strap 1406 and the second strap 1408 are adjustable. The first strap 1406 and the second strap 1408 are made from one or more of an expandable material, clothing material, thermoplastic material, plastic material, nylon material, and combinations of the same.

The first portion 1402 includes compression portion 1418 an anchor portion 1412, e.g., holder, configured to support a portion of the secondary device 1401. In this embodiment, the anchor portion 1412 includes a raised portion 1414 extending from each side and a slot 1416 configured to receive a portion of the secondary device 1401. The anchor portion 1414 and may include any anchor portion described herein.

The anchor 1414 is coupled to a compression device 1418. The compression device 1418 can include a malleable gel type material. The compression portion is adjustable in a vertical direction and configured to mechanically add more or less pressure via adjustments of the rotation devices, e.g., a first rotation device 1420, a second rotation device 1422 and a shaft 1424 with threads. The first rotation device 1420 and second rotation device 1422 allow the compression device 1418 and anchor portion 1412 to move from a first position to a second position vertically. The first rotation device 1420 and second rotation device 1422 can lock the compression device 1418 and anchor portion 1412 in a fixed position.

FIGS. 16A-16D illustrates an exemplary top plan view of the device of FIG. 14 in different use orientations.

Figures 16A, 16B:
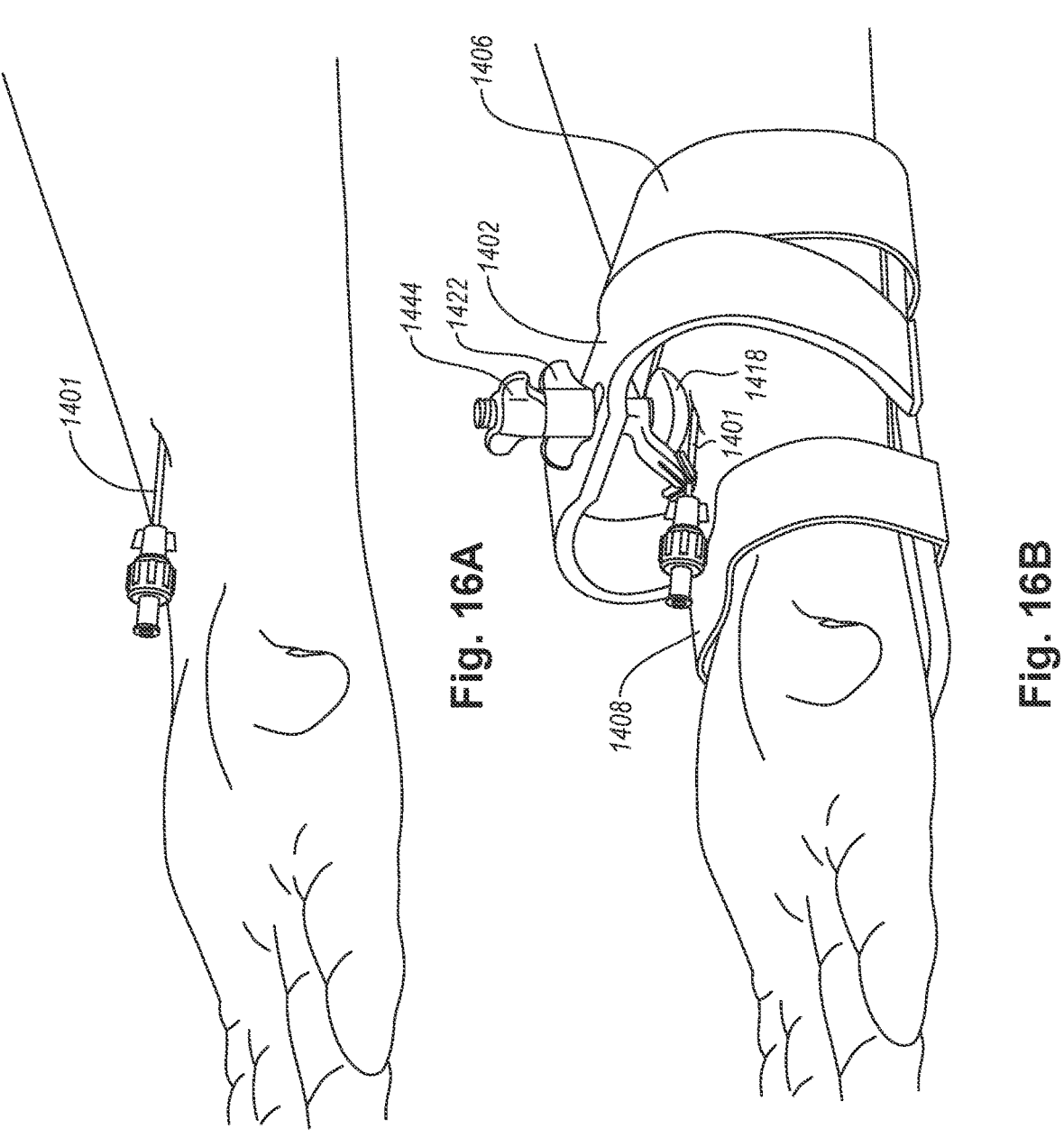
FIGS. 16A-16D illustrate an exemplary top plan view of a FIG. 14 in different use orientations.
Figures 16C, 16D:
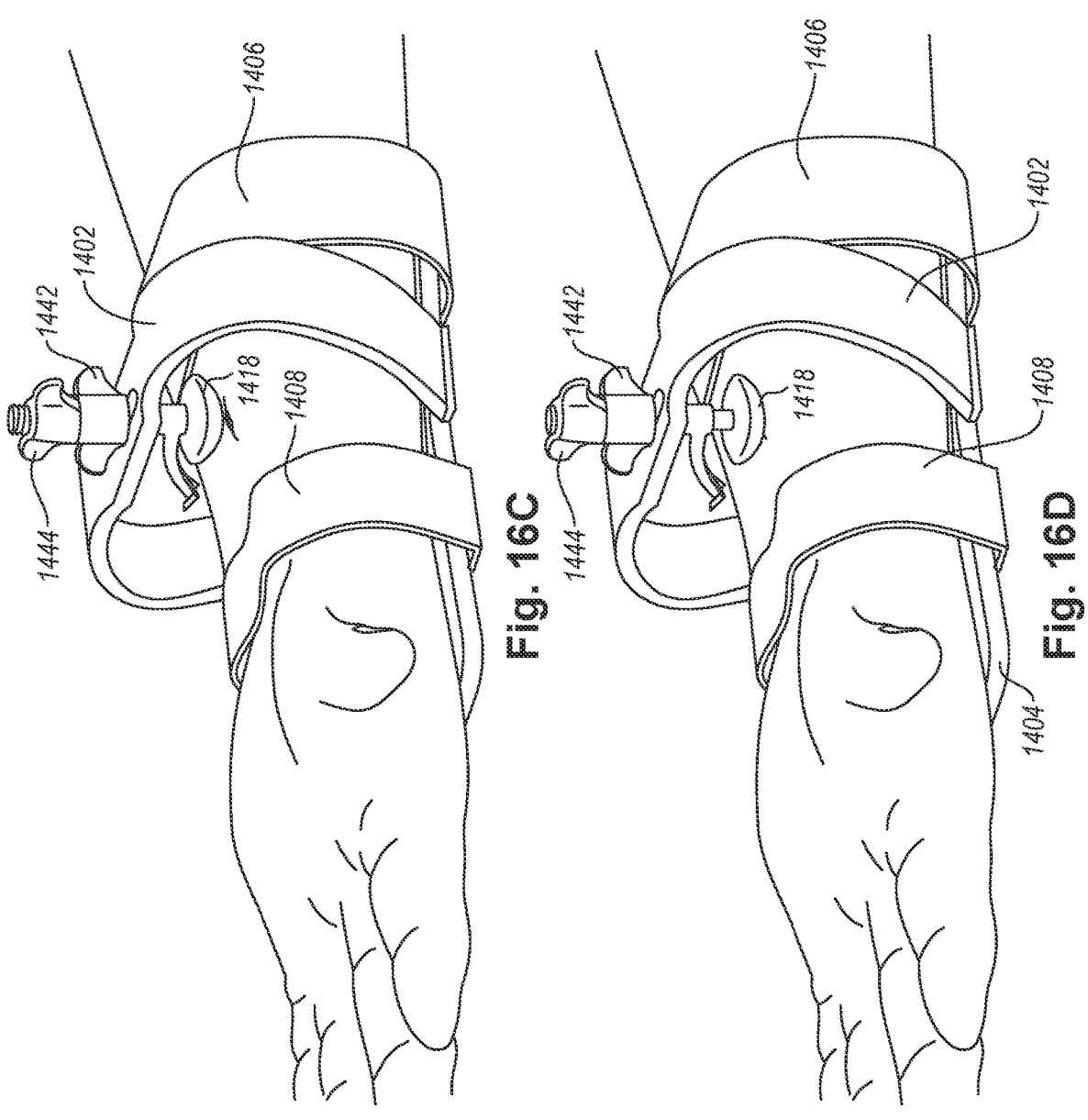

Referring to FIGS. 16A-16D, the secondary device 1401 is inserted into a sterile zone of a patient's situs (FIG. 16A). The medical device 1600 is arranged over a patient's wrist with the first strap 1406 and the second strap 1408 shown in FIG. 16B. The first rotation device 1422 and the second rotation device 1424 are adjusted to secure the secondary device 1401 (FIG. 16B). Then the procedure is completed and the secondary device 1401 is removed from the patient and the releasable liner is removed from the surface of the device (FIG. 16C).

The first rotation device 1422 and the second rotation device 1424 are adjusted to allow the compression device 1418 to put pressure on or near the wound as shown in FIG. 16D.

Figure 17:
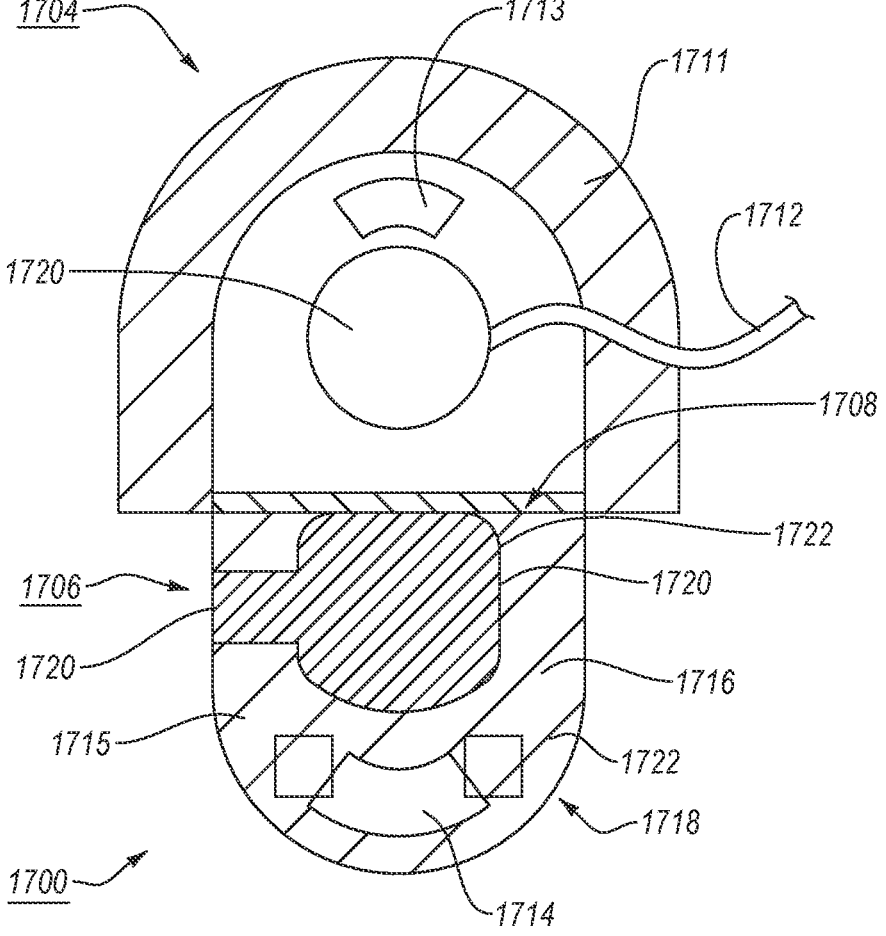
FIG. 17 illustrates an exemplary top plan view of a medical device according to another embodiment of the invention.

FIG. 17 illustrates an exemplary top plan view of a medical device according to another embodiment of the invention.

Referring to FIG. 17, the medical device is generally depicted with reference to number 1700. The device 1700 is in the form of a patch configured to be adhered to a patient. The device 1700 is configured to hold at least a portion of a secondary device (not shown) and is also configured as a compression system. The device 1700 allows the user to preserve a sterile field in use. In this embodiment, there is no strap that goes around a wrist of a patient, hand of a patient or other anatomy of the patient.

The device 1700 has a first portion 1704 and a second portion 1706. The first portion 1704 is coupled to the second portion 1706 with a hinge portion 1708, e.g., fold portion living hinge as described herein. The first portion 1704 is sized larger than the second portion 1706 and includes an adhesive portion 1711 configured to adhere to a patient's skin.

The first portion 1704 includes a compression mechanism 1720 as described herein with an inflation tube or port 1712 through which air or fluid can be passed to inflate an expandable member. The first portion 1704 includes an adhesive material 1713 configured to adhere to a portion of the second portion 1706. The first portion 1704 includes a first portion attachment mechanism 1713 configured to couple to a second portion attachment mechanism 1714 in a releasable manner.

The second portion 1706 includes an anchor portion or cutout 1722, e.g., holder, configured to support a portion of the secondary device (not shown). In this embodiment, the anchor portion 1722 includes a recessed portion a portion of the secondary device. The anchor portion 1722 may include any anchor portion described herein.

The second portion 1706 includes a first surface 1716 and a second opposite surface 1718. The first surface 1716 includes a sterile adhesive portion 1715 configured to adhere to the first portion 1704 in a non-releasable manner. The second surface 1718 includes a second sterile adhesive portion (not shown) configured to adhere to the skin of a patient in a releasable manner.

The second portion 1706 includes a cutout region 1722 with a geometry configured to provide access to a puncture site. The cutout 1722 gives access to a patient's skin and the puncture site where the secondary device is going to be inserted into a patient's artery or vein. The cutout 1722 can be any geometry, e.g., circle, square, triangle, diamond, combinations of the same and the like.

In this embodiment, the first portion 1704 and/or the second portion 1706 are coupled together with the first attachment mechanism 1713 and the second attachment mechanism 1714. The first attachment mechanism 1713 and the second attachment mechanism 1714 can include snaps, Velcro, adhesive, buckles, fasteners, combinations of the same and the like. In this embodiment, the first attachment mechanism 1713 includes a partial half circle geometry that is raised and configured to fit within a recessed portion of the second attachment mechanism 1714 in a releasable or non-releasable manner.

Figure 18:
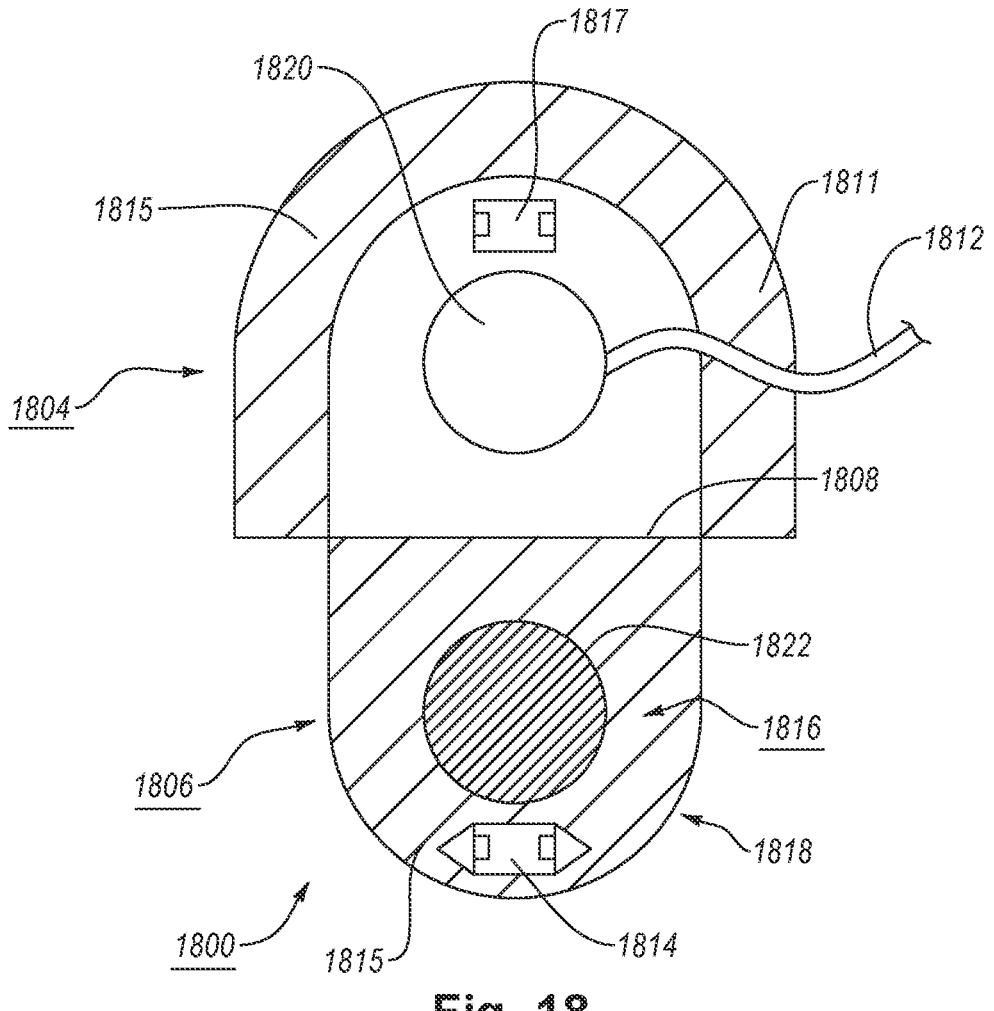
FIG. 18 illustrates an exemplary top plan view of a medical device according to another embodiment of the invention.

FIG. 18 illustrates an exemplary top plan view of a medical device according to another embodiment of the invention.

Referring to FIG. 18, the medical device is generally depicted with reference to number 1800. The device 1800 is in the form of a patch configured to be adhered to a patient. The device 1800 is configured to hold at least a portion of a secondary device (not shown) and is also configured as a compression system. The device 1800 allows the user to preserve a sterile field in use. In this embodiment, there is no strap that goes around a wrist of a patient, hand of a patient or other anatomy of the patient.

The device 1800 has a first portion 1804 and a second portion 1806. The first portion 1804 is coupled to the second portion 1806 with a hinge portion 1808, e.g., fold portion living hinge as described herein. The first portion 1804 is sized larger than the second portion 1806 and includes an adhesive portion 1811 configured to adhere to a patient's skin.

The first portion 1804 includes a compression mechanism 1820 as described herein with an inflation tube or port 1812 through which air or fluid can be passed to inflate the expandable member. The first portion 1804 includes an adhesive material 1815 configured to adhere to a portion of a patient's skin. The first portion 1804 includes a first portion attachment mechanism 1817 configured to be coupled with a second portion attachment mechanism 1814 in a releasable manner.

The second portion 1806 includes an anchor portion 1814, e.g., holder, configured to support a portion of the secondary device (not shown) and also configured to couple with the first portion attachment mechanism 1817. In this embodiment, the anchor portion 1814 includes a portion configured to receive a portion of the secondary device in a releasable manner. The anchor portion 1814 may include any type of anchor portion described herein. Moreover, the anchor portion is configured to work with anchor 1817 on the first portion.

The second portion 1806 includes a first surface 1816 and a second opposite surface 1818. The first surface 1816 includes a sterile adhesive portion 1815 configured to adhere to the first portion 1804 in a non-releasable manner. The second surface 1818 includes a second sterile adhesive portion (not shown) configured to adhere to the skin of a patient in a releasable manner.

The second portion 1806 includes a cutout region 1822 with a geometry configured to provide access to a puncture site. The cutout 1822 gives access to a patient's skin and the puncture site where the secondary device is going to be inserted into a patient's artery or vein. The cutout 1822 can be any geometry, e.g., circle, square, triangle, diamond, combinations of the same and the like.

In this embodiment, the first portion 1804 and/or the second portion 1806 are coupled together with the first attachment mechanism 1817 and the second attachment mechanism 1814. The first attachment mechanism 1817 and the second attachment mechanism 1814 can include snaps, Velcro, adhesive, buckles, fasteners, combinations of the same and the like. In this embodiment, the first attachment mechanism 1713 includes a partial rectangle geometry that is raised and configured to fit within a recessed portion of the second attachment mechanism 1814 in a releasable or non-releasable manner.

Figure 19A:
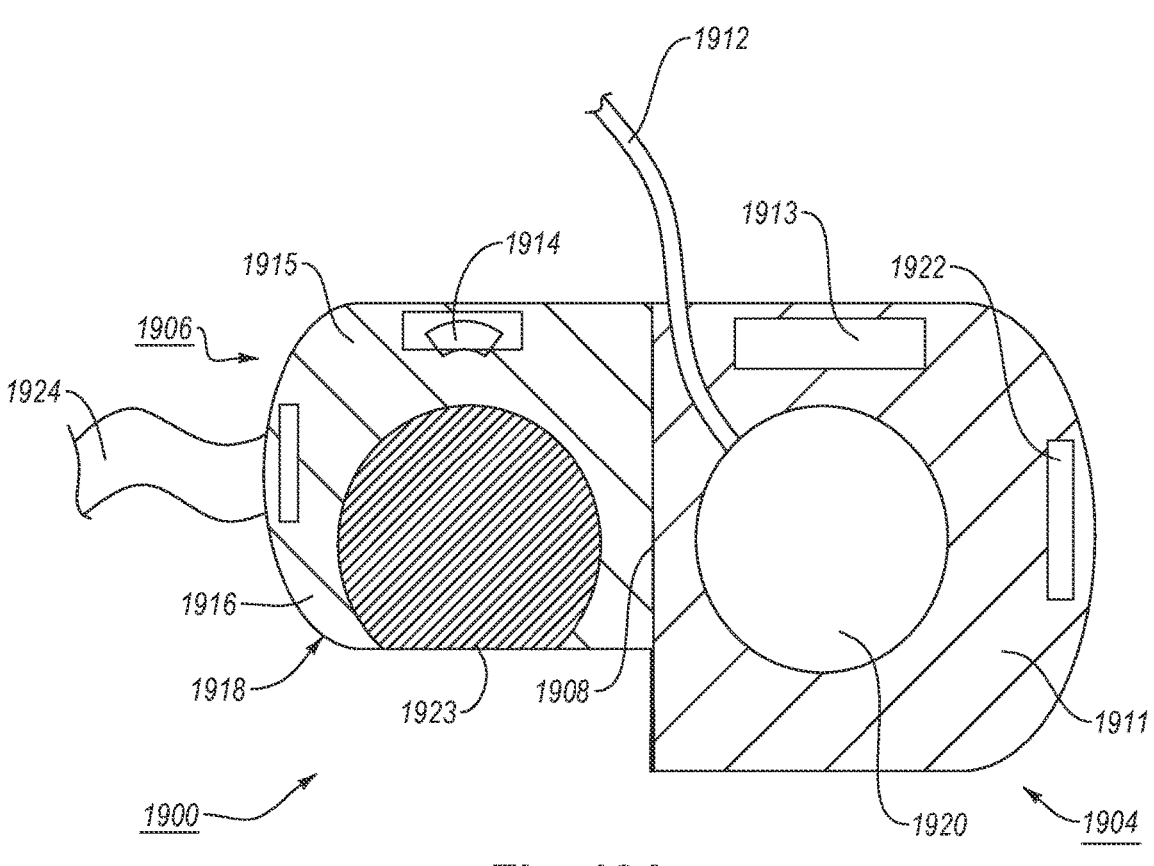
FIG. 19A illustrates an exemplary top plan view of a medical device according to another embodiment of the invention.
Figure 19B:
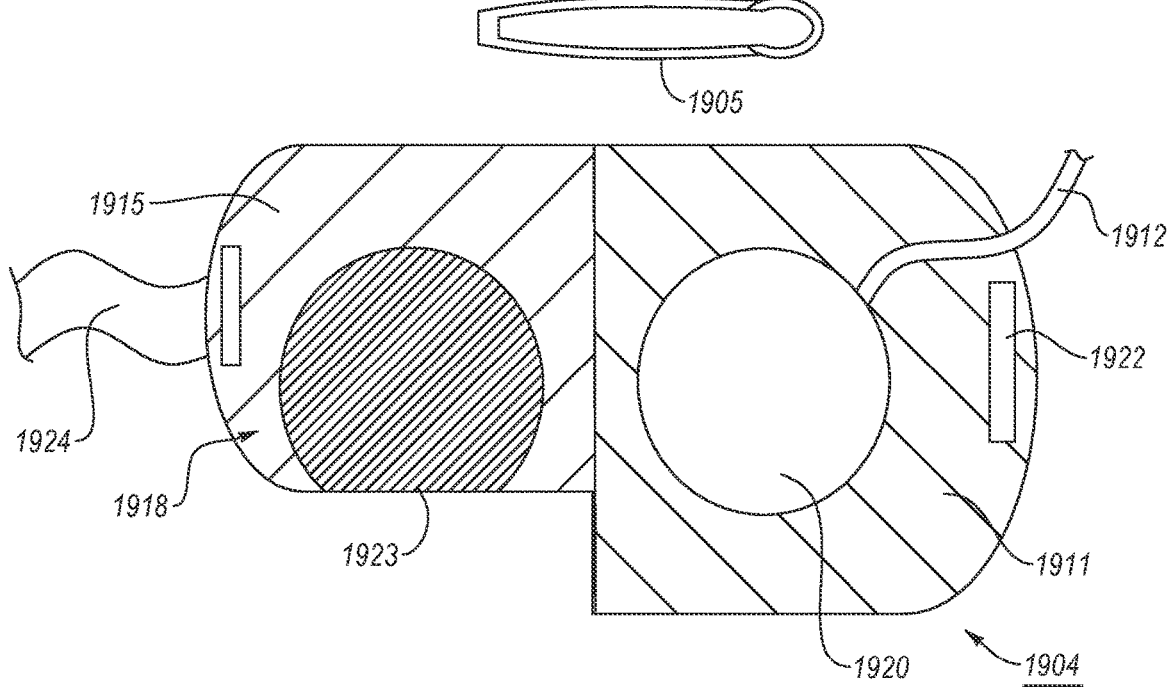
FIG. 19B illustrates an exemplary top plan view of a medical device according to another embodiment of the invention.

FIG. 19 illustrates an exemplary top plan view of a medical device according to another embodiment of the invention.

Referring to FIG. 19, the medical device is generally depicted with reference to number 1900. The device 1900 is in the form of a patch configured to be adhered to a patient. The device 1900 is configured to hold at least a portion of a secondary device (not shown) and also configured as a compression system. The device 1900 allows the user to preserve a sterile field in use. In this embodiment, there is no strap that goes around a wrist of user, hand of a user or other anatomy of the patient.

The device 1900 has a first portion 1904 and a second portion 1906. The first portion 1904 is coupled to the second portion 1906 with a hinge portion 1908, e.g., fold portion living hinge as described herein. The first portion 1904 is sized larger than the second portion 1904 and includes an inner adhesive portion 1911 sized and configured to adhere to a patient's skin and the second portion 1906.

The first portion 1904 includes a compression mechanism 1920 as described herein with an inflation tube or port 1912 through which air or fluid can be passed to inflate an expandable member. The first portion 1904 includes a first portion attachment mechanism 1913 configured to couple to a second portion attachment mechanism 1914 in a releasable manner.

The second portion 1906 includes an anchor portion 1914, e.g., holder, configured to support a portion of the secondary device (not shown) and also configured to couple with the first portion attachment mechanism 1913. In this embodiment, the anchor portion 1914 includes a portion configured to receive a portion of the secondary device in a releasable manner. The anchor portion 1914 may include any anchor portion described herein. Moreover, the anchor portion is configured to work with anchor 1913 on the first portion.

The second portion 1906 includes a first surface 1916 and a second opposite surface 1918. The first surface 1916 includes a sterile adhesive portion 1915 configured to adhere to the first portion 1904 in a non-releasable manner. The second surface 1918 includes a second sterile adhesive portion (not shown) configured to attach to the skin of a patient in a releasable manner.

The second portion 1906 includes a cutout region 1923 with a geometry configured to provide access to a puncture site. The cutout 1923 gives access to a patient's skin and the puncture site where the secondary device is going to be inserted into a patient's artery or vein. The cutout 1923 can be any geometry, e.g., circle, square, triangle, diamond, combinations of the same and the like.

In this embodiment, the first portion 1904 and/or the second portion 1906 are coupled together with the first attachment mechanism 1913 and the second attachment mechanism 1914. The first attachment mechanism 1913 and the second attachment mechanism 1914 can include snaps, Velcro, adhesive, buckles, fasteners, combinations of the same and the like. In this embodiment, the first attachment mechanism 1913 includes a partial raised rectangle geometry that is configured to fit within a recessed portion of the second attachment mechanism 1914 in a releasable or non-releasable manner.

The first portion 1904 includes an opening 1922 configured to receive a portion of a strap 1924, e.g., Velcro strap that is coupled to the second portion 1906. The strap 1924 is sized to fit around a wrist of patient in a releasable manner to secure the device 1900 to the patient.

Figure 20A:
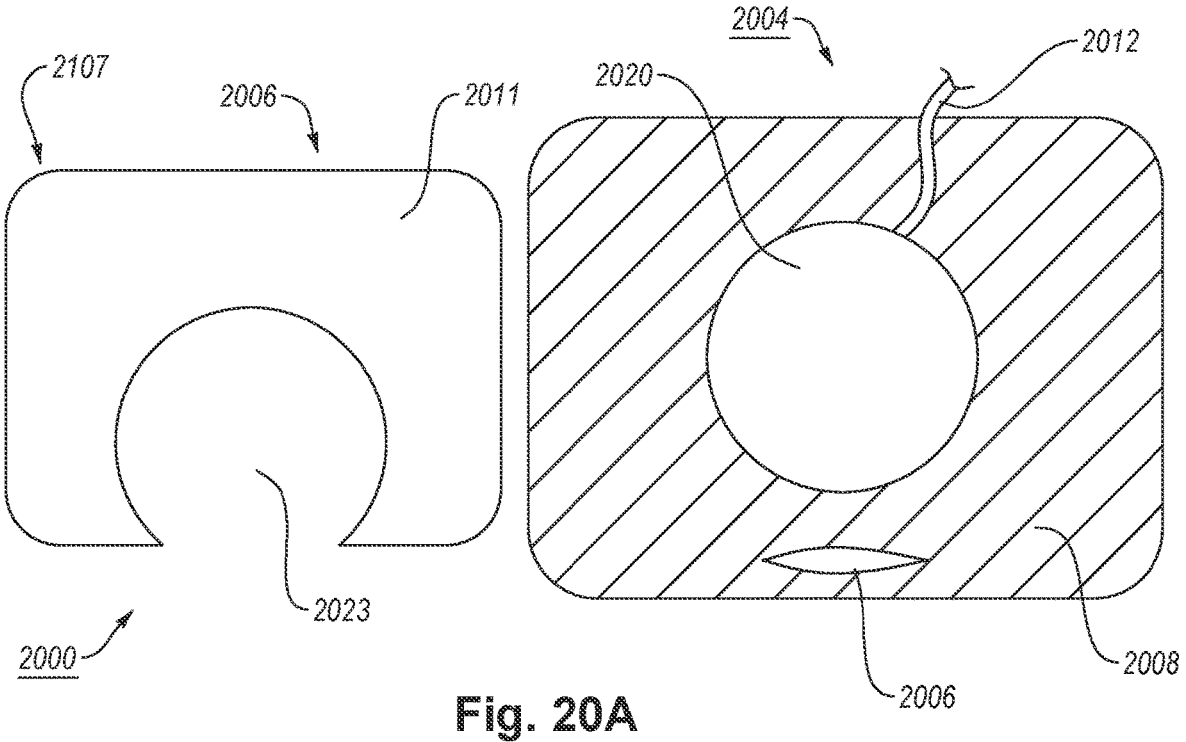
FIG. 20A illustrates an exemplary top plan view of a medical device according to another embodiment of the invention.
Figure 20B:
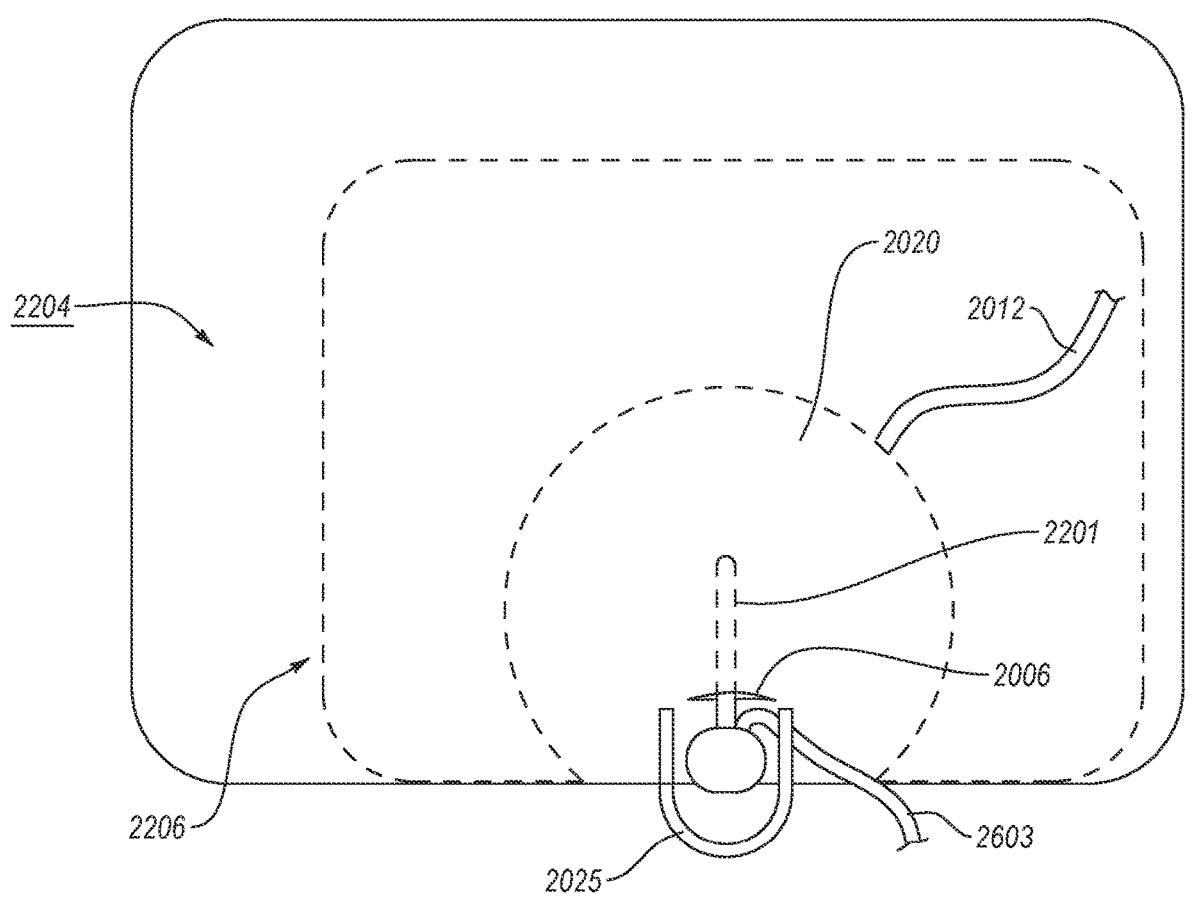
FIG. 20B illustrates an exemplary top plan view of the medical device of FIG. 20A in a different orientation.

FIG. 20A illustrates an exemplary top plan view of a medical device according to another embodiment of the invention. FIG. 20B illustrates an exemplary top plan view of the medical device of FIG. 20A in a different orientation.

Referring to FIGS. 20A-20B, the medical device is generally depicted with reference to number 2000. The device 2000 is in the form of a transparent patch configured to be adhered to a patient. The device 2000 is configured to hold at least a portion of a secondary device and also configured as a compression system. The device 2000 allows the user to preserve a sterile field in use.

Optionally, the device 2000 includes an optional strap (not shown) configured to be adjustable around the patient's wrist and configured to support and hold the device in place. In a preferred embodiment, there is no strap and the device is set forth as a patch device that resides solely on one side of a patient's wrist. The device 2000 is positioned such that it fits over an inside portion of the patient's wrist.

The device 2000 has a first portion 2004 and a second portion 2006. The first portion 2004 is not connected to the second portion 2006. However, optionally, the first portion 2004 may be connect to the second portion 2006 with a hinge portion as described herein.

The second portion 2006 does not include an anchor portion configured to support a portion of the secondary device 2001. Optionally and/or alternatively, the second portion 2006 can include an anchor portion as described herein.

The second portion includes a sterile adhesive portion (not shown) on the second surface 2107 opposite the first surface 2111. The sterile adhesive portion is configured to the skin of a patient in a releasable manner. The second portion 2006 includes a cutout region 2023 in a partial half circle geometry. The cutout 2023 gives access to a patient's skin and the puncture site where the secondary device will be inserted into a patient's artery or vein. The cutout 2023 can be any geometry, e.g., circle, square, triangle, diamond, combinations of the same and the like.

The second portion 2006 includes a cutout region 2023 in a partial half circle geometry. The cutout 2023 gives access to a patient's skin and the puncture site where the secondary device will be inserted into a patient's artery or vein. The cutout 2023 can be any geometry, e.g., circle, square, triangle, diamond, combinations of the same and the like.

The first portion 2104 includes a compression mechanism 2020. In this embodiment, the compression mechanism 2202 includes an expandable member configured to expand and apply pressure to a wound. The expandable member can include a balloon, capable of being inflated or deflated. In one embodiment, the expandable member includes an inflation tube or port 2012 through which air or fluid can be passed to inflate the expandable member. The balloon or bladder can include more than one balloon or bladder each configured to provide pressure to the artery as known in the art. The balloon or bladder include a transparent material and are configured to be transparent through. The first portion 2004 includes an opening 2006 configured to allow a portion of the secondary medical device to go through the first portion 2004. The first portion and second portion are also made of transparent material, e.g., thermoplastic. The adhesive is made from materials described herein and also transparent.

In this embodiment, a clamp 2025 is also used to aid in securing the secondary device during the procedure. The clamp 2025 can have any geometry with an opening at one end and a closure at a second end. Referring to FIGS. 20C-D, the clamp 2025 includes a first end 2030 and a second end 2028. The second end 2028 includes a pair of opens 2032 configured to narrow as it approaches the first end 2030. The clamp may include one opening or two openings. The clamp 2035 can also be configured with resistance or tension, e.g., memory, where the natural state is a closed.

Optionally and/or alternatively, the first portion 2104 and/or the second portion 2106 can also include a secondary attachment mechanism or mechanisms (not shown) configured to allow the first portion to releasably or non-releasably attach to the second portion. The secondary attachment mechanism can include snaps, Velcro, adhesive, buckles, fasteners, combinations of the same and the like.

In operation, the treatment area is sterilized and prepare for the procedure as known in the art. Optionally, the area is numbed, and a needle is inserted into the radial arterial as known in the art. Next, a guidewire is inserted through the needle as known in the art. A sheath or catheter in the artery as known in the art. The area around the sheath or catheter is cleaned and any blood is wiped away.

The first portion 2004 is arranged over the first portion and attached with adhesive to the patient and the first portion. Optionally only a portion of the adhesive is used and the peel away material is dimension to allow for multiple regions of adhesive protection, e.g., any pattern of adhesive 2008 may be exposed. The sheath is placed through the hole 2006 of the first portion. The hole and first portion and optionally an anchor (not shown) are used to secure the sheath in the procedure. The sheath 2001 is secured to prevent the sheath from moving in and out and traumatizing the artery. Optionally and/or alternatively, a clamp 2025 is further used to secure a flush port 2003 of the sheath 2001 to the medical device. The clamp can be used in any of the devices described herein to secure the sheath and/or flush port. Each of the sheaths described herein include a flush port.

After the procedure has been completed the sheath 2001 is removed and the first portion 2004 is fully attached to the second portion 2006 and to the patient. Pressure is applied with the balloon to cause the desired degree of hemostasis and stop the bleeding. The transparent nature of the device allows the clinician to view the wound and blood to ensure the desired degree of hemostasis.

Figure 21A:
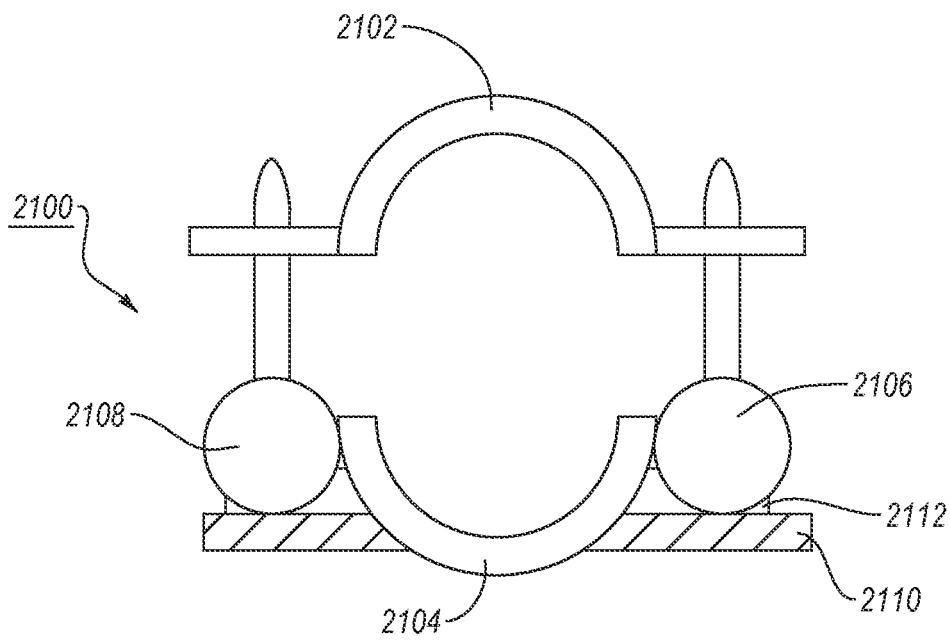
FIG. 21A illustrates an exemplary magnified side plan view of an anchor portion according to another embodiment of the invention in an open orientation.
Figure 21B:
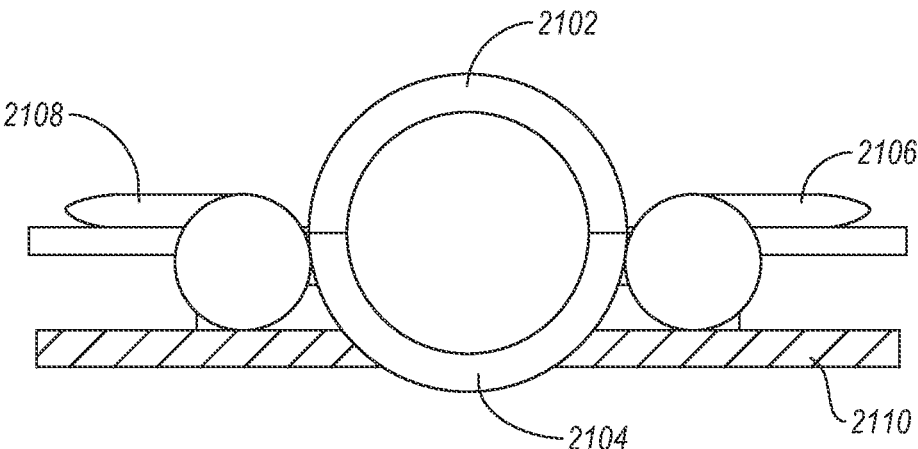
FIG. 21B illustrates an exemplary magnified side plan view of the anchor portion according to FIG. 21A in a closed orientation.

FIG. 21A illustrates an exemplary magnified side plan view of an anchor portion according to another embodiment of the invention in an open orientation. FIG. 21B illustrates an exemplary magnified side plan view of the anchor portion according to FIG. 21A in a closed orientation.

Referring to FIGS. 21A-21B, the anchor portion is generally depicted with reference to number 2100. The anchor portion 2100 is configured to releasably secure at least a portion of a secondary device, e.g., sheath. The anchor portion 2100 includes an upper clamp region 2102 coupled to a lower clamp region 2104 with a first locking mechanism 2106 and a second locking mechanism 2108. Upon rotation of the first locking mechanism 2106 and the second locking mechanism 2108 the upper clamp is squeezed unto the lower clamp 2104.

The anchor portion 2100 is secured to any medical device 2110 with an adhesive material 2112 or other attachment means. The other attachment means may include plastic molding techniques or other techniques as known in the art. The upper clamp 2102 and lower clamp 2104 include a curved region or recessed portion to receive a portion of the secondary attachment device. The medical device 2110 may include any medical device described herein.

Figure 22:
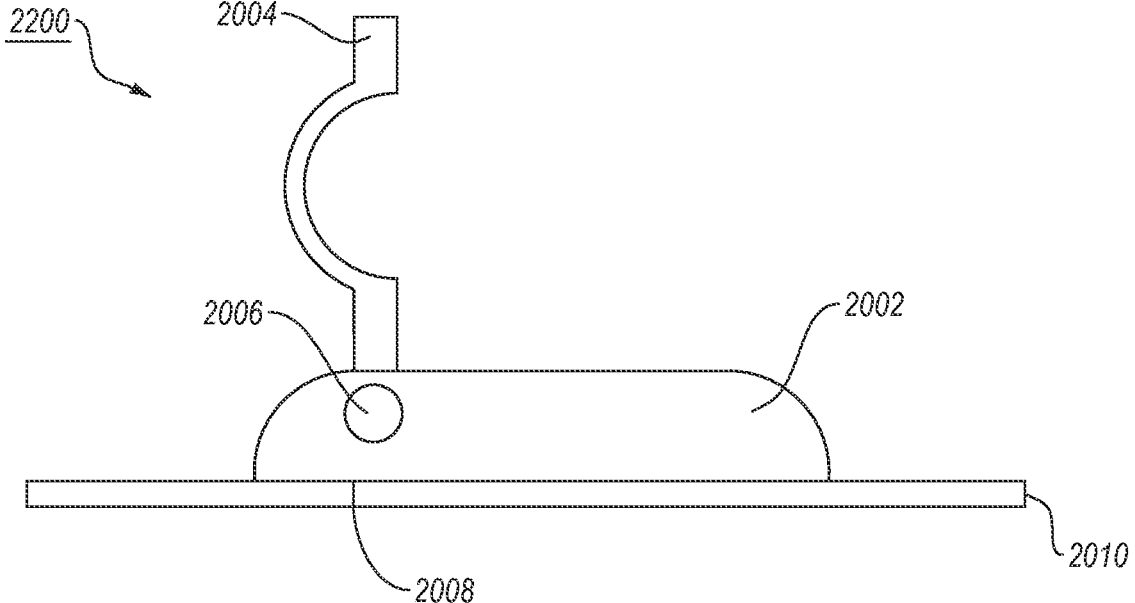
FIG. 22 illustrates an exemplary magnified side plan view of an anchor portion according to another embodiment of the invention in an open orientation.

FIG. 22 illustrates an exemplary magnified side plan view of an anchor portion according to another embodiment of the invention in an open orientation.

Referring to FIG. 22, the anchor portion is generally depicted with reference to number 2200. The anchor portion 2200 is configured to releasably secure the at least a portion of a secondary device (not shown). The anchor portion 2200 includes an upper clamp region 2204 coupled to a lower clamp region 2202 with a hinge 2206 that allows the upper clamp to pivot from an open to a closed position. In the closed position the upper clamp 2204 is locked into place with the lower clamp region 2202 with a locking clamp, e.g., pressure fit portion (not shown). The upper clamp 2204 and lower clamp 2202 can include a curved region or recessed portion to receive a portion of the secondary attachment device (not shown). The medical device 2210 can include any medical device described herein. The lower clamp 2202 is attached to the medical device 2210 with an adhesive or other attachment mechanism as known in the art.

Reference throughout the specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout the specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

It is understood that the above-described embodiments are only illustrative of the application of the principles of the present invention. The present invention may be embodied in other specific forms without departing from its spirit or essential characteristics. The described embodiment, including the best mode, is to be considered in all respects only as illustrative and not restrictive. The scope of the invention is, therefore, indicated by the appended claims, if any, in conjunction with the foregoing description.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The inventions and methods described herein can be viewed as a whole, or as a number of separate inventions, that can be used independently or mixed and matched as desired. All inventions, steps, processed, devices, and methods described herein can be mixed and matched as desired. All previously described features, functions, or inventions described herein or by reference may be mixed and matched as desired.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of using a surgical patch for supporting a secondary medical device including a sheath during a non-invasive surgical procedure using a radial artery and for providing patent hemostasis to the radial artery after the non-invasive surgical procedure, comprising:

providing a medical device comprising a transparent medical device including a first portion including a compression bladder in fluid communication with an inflation port or tube, a first adhesive material arranged on the first portion under a first peel away sheet; and a second portion movably coupled to the first portion with a living hinge, the second portion including a second adhesive material arranged under a second peel away sheet, and a cut out region configured to allow access to a puncture site of a patient, wherein the first portion is larger than the second portion;

removing the second peel away sheet, on the second portion, to expose the second adhesive material;

attaching the second portion with the second adhesive material to a wrist of the patient such that the cut out region is arranged partially around or in close proximity to the sheath located at least partially in the radial artery of the patient;

at least partially supporting the sheath with an anchor portion;

removing the sheath;

removing the first peel away sheet to expose the first adhesive material;

attaching the first portion to the second portion with the first adhesive material; and at least partially inflating the compression bladder to a predetermined pressure to provide a desired degree of hemostasis to the radial artery.

2. The method of claim 1, wherein the second portion further comprises a strap and the first portion comprises a slot to receive a portion of the strap and further comprising releasably attaching the strap with the slot around the wrist of the patient.

3. The method of claim 2, wherein the strap comprises hook material on one side and loop material on a second opposite side.

4. The method of claim 1, wherein the first portion further comprises a compression pad arranged on the compression bladder.

5. The method of claim 4, wherein the compression pad comprises a hemostatic agent.

6. The method of claim 1, wherein the first portion and the second portion comprise a transparent material.

7. The method of claim 6, wherein the transparent material comprises a thermoplastic material.

8. The method of claim 6, wherein the transparent material comprises a plastic material.

9. The method of claim 1, wherein the medical device is a sterile or sterilized medical device.

10. The method of claim 1, wherein the medical device further comprises a clamp and further comprising releasably attaching the clamp to the first portion or a flush port of the sheath.

11. The method of claim 1, further comprising a pump.

12. The method of claim 11, wherein the inflating the compression bladder to a predetermined pressure to provide a desired degree of the hemostasis to the radial artery comprises operating the pump.

13. The method of claim 1, wherein the first portion further comprises a first clamp and the second portion further comprises a second clamp, wherein the first clamp is configured to be releasably attached to the second clamp further comprising releasably attaching the first clamp to the second clamp.

14. The method of claim 13, wherein the first clamp comprises a protrusion and the second clamp comprises a recess configured to receive the protrusion.

15. The method of claim 1, wherein the living hinge comprises one or more of a stamped region, a perforated region, and a thinned region.

16. The method of claim 1, wherein the first portion comprises a sterile gauze material configured to absorb blood.

17. The method of claim 1, wherein the second portion comprises a sterile gauze material configured to absorb blood.

18. A method of using a surgical patch for supporting a secondary medical device including a sheath during a non-invasive surgical procedure using a radial artery and for providing patent hemostasis to the radial artery after the non-invasive surgical procedure, comprising:

providing a medical device comprising a transparent thermoplastic medical device including a first portion including a compression bladder in fluid communication with an inflation port or tube, a first adhesive material arranged on the first portion under a first peel away sheet, and a compression pad arranged on the compression bladder, wherein the compression pad comprises a hemostatic agent; and a second portion movably coupled to the first portion with a living hinge comprising a stamped region, the second portion including a second adhesive material arranged under a second peel away sheet, a cut out region configured to allow access to a puncture site of a patient, and an anchor portion configured to support the sheath, wherein the first portion is larger than the second portion and wherein the second portion comprises a sterile gauze material configured to absorb blood;

removing the second peel away sheet, on the second portion, to expose the second adhesive material;

attaching the second portion with the second adhesive material to a wrist of the patient such that the cut out region is arranged partially around the sheath located at least partially in the radial artery of the patient;

at least partially supporting the sheath with the anchor portion during the non-invasive surgical procedure;

removing the sheath;

removing the first peel away sheet to expose the first adhesive material;

attaching the first portion to the second portion with the first adhesive material such that the compression pad is positioned directly over the puncture site; and inflating the compression bladder with a pump to a predetermined pressure to provide hemostasis to the radial artery within 15 minutes or less.

* * * * *